US011065297B2

(12) United States Patent
McIntosh et al.

(10) Patent No.: US 11,065,297 B2
(45) Date of Patent: Jul. 20, 2021

(54) METHOD AND FORMULATION FOR INHALATION

(71) Applicant: Monash University, Clayton (AU)

(72) Inventors: Michelle McIntosh, Parkville (AU); David Morton, Parkville (AU); Tomas Sou, Parkville (AU); Livesey Olerile, Parkville (AU); Richard Prankerd, Parkville (AU)

(73) Assignee: MONASH UNIVERSITY, Clayton (AU)

( * ) Notice: Subject to any disclaimer, the term of this patent is extended or adjusted under 35 U.S.C. 154(b) by 0 days.

(21) Appl. No.: 15/343,408

(22) Filed: Nov. 4, 2016

(65) Prior Publication Data

US 2017/0224762 A1 Aug. 10, 2017

Related U.S. Application Data

(63) Continuation of application No. 14/236,465, filed as application No. PCT/AU2011/001430 on Nov. 7, 2011.

(30) Foreign Application Priority Data

Aug. 1, 2011 (AU) ................................ 2011903049

(51) Int. Cl.

| | |
|---|---|
| ***A61K 38/00*** | (2006.01) |
| ***C07K 7/16*** | (2006.01) |
| ***A61K 38/095*** | (2019.01) |
| ***A61K 9/16*** | (2006.01) |
| ***A61K 9/00*** | (2006.01) |

(52) U.S. Cl.

CPC .......... *A61K 38/095* (2019.01); *A61K 9/0073* (2013.01); *A61K 9/0075* (2013.01); *A61K 9/1617* (2013.01); *A61K 9/1623* (2013.01); *A61K 9/1652* (2013.01); *C07K 7/16* (2013.01)

(58) Field of Classification Search

None

See application file for complete search history.

(56) References Cited

U.S. PATENT DOCUMENTS

| | | | | | |
|---|---|---|---|---|---|
| 7,807,200 | B2 * | 10/2010 | Lipp | A61K 9/0073 | 424/489 |
| 2006/0088479 | A1 * | 4/2006 | Whitfield | A61K 9/0075 | 424/46 |
| 2011/0171312 | A1 * | 7/2011 | Kuo | A61K 9/14 | 424/489 |
| 2011/0237508 | A1 * | 9/2011 | Amorij | A61K 38/11 | 514/10.9 |

OTHER PUBLICATIONS

Anderson et al., Am. Fam. Physician 75:875-882 (2007).*

Gimpl et al., Physiol. Rev. 81:629-683 ay p. 631, col. 1, 1st paragraph, Table 1 (2001) (Year: 2001).*

Margo, K., "Development of polymer-based spray dried particles and cohesion evaluation," abstract of oral presentation, Monash University Faculty of Pharmacy and Pharmacy and Pharmaceutical Honours Presentations, 1 page, (Apr. 7, 2010) (Year: 2010).*

National Center for Biotechnology Information, PubChem Compound Database, CID=439302, http://pubchem.ncbi.nlm.nih.gov/compound/439302, 51 pages (accessed on Aug. 24, 2015) (Year: 2015).*

Sawyer et al., Annu. Rev. Pharmacol. 13:5-17 at p. 5, 2nd paragraph (1973) (Year: 1973).*

Su et al., Cochrane Database of Systematic Reviews, Issue 3, Art. No. CD005457, pp. 1-35 at p. 3, col. 1, last full paragraph (2007) (Year: 2007).*

World Health Organization, "WHO Recommendations for the Prevention and Treatment of Postpartum Hemorrhage", available online http://apps.who.int/iris/bitstream/10665/75411/1/9789241548502_eng.pdf, 48 pages, at p. 4, 1st paragraph (2012) (Year: 2012).*

Nassta, G., "Development, Characterisation and Evaluation of Oxytocin Spray Dried Particles," abstract of oral presentation, Monash University Faculty of Pharmacy and Pharmacy and Pharmaceutical Honours Presentations, 1 page, (Apr. 7, 2010), (Year: 2010).*

"Derivative", Biology Online, available online at https://www.biology-online.org/dictionary/Derivative, 1 page (accessed on Feb. 18, 2020) (Year: 2020).*

Seville et al., Powder Technol. 178:40-50 (2007) (Year: 2007).*

* cited by examiner

*Primary Examiner* — Thea D' Ambrosio

(74) *Attorney, Agent, or Firm* — Honigman LLP; Kelly T. Murphy; Jonathan P. O'Brien

(57) ABSTRACT

This invention relates to drug delivery and in particular to the delivery of biologically active agents in the form of dry powders for inhalation. The invention also relates to methods for preparing such dry powder formulations and methods for their use.

14 Claims, 16 Drawing Sheets

Delay
Seconds
300
200
100
0
*

Initial burst
Seconds
300
200
100
0

Bursts/30min
25
20
15
10
5
0

Total duration
Minutes
150
100
50
0
*
Post-partum
Airway delivery
Intramuscular injection

METHOD AND FORMULATION FOR INHALATION

CROSS-REFERENCE TO RELATED APPLICATIONS

This application is a continuation application of U.S. Ser. No. 14/236,465, filed Jun. 18, 2014, which claims priority under 35 U.S.C. § 371 to Patent Cooperation Treaty Application No. PCT/AU2011/001430, filed Nov. 7, 2011, which claims the benefit of earlier filed Australian Patent Application No. 2011903049, filed Aug. 1, 2011, the entire contents of which are incorporated herein by reference in their entirety.

This invention relates to drug delivery and in particular to the delivery of biologically active agents in the form of dry powders for inhalation. The invention also relates to methods for preparing such dry powder formulations and methods for their use.

Every year, over 150,000 women, mostly in developing countries, die due to postpartum haemorrhage. This condition is largely preventable with the administration of uterotonic drugs, such as oxytocin, in the third stage of labour. The World Health Organisation has endorsed oxytocin as the most effective therapy in the treatment of postpartum haemorrhage. The use of oxytocin in developing countries presents several difficulties. Oxytocin is a peptide with relatively poor stability in solution. This then requires refrigerated storage, for example at 2-8° C., which is problematic in developing countries. An additional consideration with the use of oxytocin is that it requires sterilized needles and syringes and trained personnel for administration, another requirement that cannot be guaranteed in developing nations. Hence, a problem to be solved is the development of a system for effective and inexpensive delivery of oxytocin for appropriate use in developing counties, in order to prevent deaths in childbirth due to PPH. One possible solution to this problem may be to create a dry powder pulmonary delivery system, suitable for effective and affordable administration of oxytocin, or other biologically active peptides or proteins, that is suitable for use in remote and environmentally demanding regions of developing nations.

Pulmonary delivery has been proposed to be a suitable systemic route for biological agents such as peptides, proteins, vaccines, and nucleic acid based agents. The challenges in delivering such large macromolecules are substantial and result in a broad and major uncertainty and risk as to the possibility of success. The challenges begin with the generation of an aerosol of appropriate dose which is suitable for efficient and consistent deep lung delivery. If such suitable delivery can be achieved, the material must dissolve or become available in such a form that can be transported across the biological membranes and other barriers such as surfactant and mucosal interfaces. Dissolution kinetics will determine the extent of solubilisation, and this would be expected to be hindered by hydrophobic formulations and hence material be subjected to pulmonary clearance timescales before being taken up systemically, as outlined by O'Donnel and Smythe in "Controlled Pulmonary Drug Delivery", published by Springer 2011, ISBN 978-1-4419-9744-9. Before a macromolecule can be transported into the systemic circulation, it must then be able to survive an onslaught from the body defence mechanisms, including from the mucociliary escalator, from peptidases and from macrophages. These challenges are clearly reviewed and outlined in the recent expert text, "Controlled Pulmonary Drug Delivery", published by Springer 2011, ISBN 978-1-4419-9744-9. For example, it is concluded by Olsson et al. that "for systemic targets of peptides and proteins, the challenge seems to be to achieve absorption at a rate that is competitive relative to the rate of clearance mechanisms in order to secure sufficient bioavailability" and "What constitute optimal characteristics in each particular case and how these may be predicted from abstracted properties remains far from clear with our present understanding". Rapid onset of action for pulmonary delivery relative to oral delivery of selected small molecules, such as less than 781 Da, which are primarily hydrophilic, has been proposed. However, for macromolecules such as peptides and proteins of molecular weight typically of the order 1000 Da and above, the onset of action is highly uncertain and likely to be hindered by a need for paracellular diffusion mechanisms. Half lives for removal from the lung epithelium into the blood via such membranes arc highly variable and uncertain, but appear typically to require several minutes and even over hundreds of minutes, as outlined by Sakagami and Gumbleton in "Controlled Pulmonary Drug Delivery", published by Springer 2011, ISBN 978-1-4419-9744-9. Hence, clearly a rapid pharmacokinetic uptake and pharmacodynamic onset of the order of one or two minutes for a peptide of the order 1000 Da and larger would not be assumed but would be surprising, from a pulmonary delivered macromolecule. It would be especially surprising if the pulmonary delivery system comprised a powder that required dissolution, and even more so if that particle had a hydrophobic surface.

Additional challenges in this context include producing a physically and chemically stable product that is maintained during production, storage and transport, and in use. It is also important for the agents not to cause bronchoconstriction. A peptide such as oxytocin, which causes uterine contractions might interact with receptors present in the pulmonary system and hence cause bronchoconstriction. It is also important for the agents not to be metabolised in the lung. If these multiple and very significant challenges can be met, pulmonary delivery can provide unique advantages, including avoiding use of needles, avoiding first pass metabolism through the oral route, and extra stability offered by powdered formulations.

Spray drying has been widely used for many years to produce powdered products in the areas such as food, detergent and industrial chemicals. In many cases, relatively large and free-flowing particles are produced. To a lesser extent, the technique has been adapted to generate fine and ultrafine particles, and innovation here has been led by the inorganic materials industries, such as producers of technical ceramics (T. T. Kodas, Adv. Mater., 1989, 6, 180). This approach of generating droplets from often complex solutions, to form an aerosol, and then drying these as isolated units into particles has been recognized as providing enhanced control over particle morphology, stoichiometry, purity, size as well as structure. The advantages can be viewed as a hybrid between the "top-down" and "bottom-up" approaches of particle engineering. However, the pharmaceutical industry has only relatively recently recognized the advantages of this route to engineer fine particles (R. Vehrig, Pharm Res., 2008, 25(5), 999), and recently spray-dried materials have appeared in commercially available dry powder inhaler systems. Most attention in this area has been directed to the impact of shape, density and rugosity on aerosolisation.

It is a challenge, however, to deliver drug molecules into the respiratory tract and even into the lower lung to provide a therapeutic effect, especially drugs that are solid at the temperature of administration. In this respect, whilst dry powders present an attractive means of drug delivery, generating micronized particles suitable for highly efficient aerosolisation remains a very significant technical challenge.

Upon inhalation, larger aerosolised drug particles tend to be deposited by impaction and gravitational sedimentation at the back of the throat and upper respiratory tract where they are prone to mucociliary clearance into the gastro intestinal tract and subsequent metabolism. Also, larger drug particles cannot progress deep into the lower lung due to the narrowing of the bronchioles. It is believed that for effective local aerosol transport and delivery to the respiratory system including trachea, bronchi and alveoli, particles of less than 5 μm aerodynamic diameter are preferred, while for deep lung, bronchioles and alveoli, particles of less than 3 pm are preferred especially for systemic uptake.

Whilst inhalation delivery is a desirable means, a significant technological barrier to this remains the practicality of engineering an aerosol suitable for highly efficient delivery, (e.g.: >50% dose delivery to site of treatment), reproducible delivery (e.g. having a coefficient of variation (CV %) of dose delivery <10%) and high payload (e.g. >1 mg powder delivery to site of treatment) in a practical and cost effective format comprising a device and a formulation. Dry powder delivery provides an attractive delivery format. However, generating micronized particles suitable for highly efficient aerosolisation remains a very significant technical challenge. In addition to the problems mentioned above, any practical inhalation delivery system for dry powders would need to avoid or minimise agglomeration of the particles at the time of inhalation, have low variation in delivered dose due to poor flow properties or inconsistent agglomeration, and avoid or minimise incomplete removal of the powder from the delivery device caused by adhesion of powder to the walls of the device.

In recent years a new generation of “smart” powder formulations for inhalation of biomolecules has been proposed, often formed via spray drying. In many cases, these formulations are designed empirically, and comprise a cocktail of excipients each of which is proposed to provide one or more functional roles in the solid phase. One of those excipients used in this context has been the amino acid L-leucine. The potential advantageous properties provided by adding L-leucine, either by co-milling or by condensation/precipitation, was first demonstrated by Staniforth and Ganderton et al. (See for example, WO 96/23485 and WO 00/33811). This work indicated that peculiar physical properties of this amino acid provided its performance enhancing behaviour. Several groups have since studied the benefit L-leucine provides to powder aerosolization, especially when co-sprayed with actives and excipients, however, the true nature of the structure-performance relationship in such systems remains unclear. More broadly, it also appears that certain peptides/proteins in spray dried particle structures, for example albumins, isoleucine or tri-leucine, may also confer improved aerosolization performance in use. Alternatively, lipid and fatty acid materials may also provide some benefit in this respect, such as phospholipids (for example DPPC), lecithins or fatty acid salts (for example sodium or magnesium stearate).

It has now been surprisingly found that L-leucine can be used to advantage in processes for preparing dry powders for inhalation via spray drying, and can result in the formation of suitable dry powders in circumstances where, in the absence of L-leucine, suitable particles would not form at all or would immediately coalesce or irreversibly agglomerate.

Accordingly, in a first aspect the present invention provides a method for preparing a dry powder for inhalation comprising:

preparing an aqueous solution and/or suspension comprising a biologically active protein or peptide, one or more mono, di- or polysaccharides and/or amino acids capable of forming an amorphous glass matrix, and L-leucine; and spray drying the aqueous solution or suspension to produce a dry powder suitable for inhalation.

Without wishing to be limited by theory, it is believed that the L-leucine concentrates at the surface of the formed particles, possibly due to its hydrophobicity, in such a way that the particles are stabilized and such that agglomeration is inhibited. The particles so formed have also been found to be protected from degradation, lowering of glass transition temperature and recrystallisation from atmospheric or other moisture, such that they do not require the use of a moisture-free packaging environment to the same extent as current dry powder formulations. This also allows the dry powders of the present invention to be used in remote and environmentally demanding regions of developing nations. The challenges in producing a powder containing a biological macromolecule that is suitable for inhalation, are well recognized and have been extensively reported following the failure to successfully market the Exubera inhaled insulin product. While some of the technical challenges were addressed in developing the Exubera product, it was necessary to provide a very complex, expensive and impractical inhaler device, plus the powder was extremely sensitive to moisture having to be handled in environments of very low humidity. Many additional factors contributed to its failure, including bioavailability and uncertainty in its fate in the lung. This product failure has emphasized the extreme complexity in developing a solution to the problem outlined here.

As used herein the term “amorphous glass matrix” refers to a matrix in which the biologically active protein or peptide is dispersed which is substantially non-crystalline, or has no substantial regions of crystallinity or regular repeating structural molecular order.

The solution/dispersion may include further components, including other amino acids, albumins and amino acid derivatives such as tri-leucine, which can also assist in the formation and stabilization of the dry powder formulation. Depending on the final use of the formulation, other drugs can be incorporated, including non-peptidic drugs. The biologically active protein or peptide, other drugs or other components may be in solution or suspension, and additional excipients, such as stabilizing agents, surfactants and the like can also be included.

Accordingly, as used herein, a reference to a “solution and/or suspension” or “solution/suspension” indicates a mixture of water and other components in which some components may be dissolved (i.e. in solution) and some components may be in suspension, or be in the form of a nano-suspension, emulsion or micro-emulsion. The aqueous solution may include other co-solvents in some embodiments.

The aqueous liquid may include other co-solvents in some embodiments. The term “aqueous” will be understood to refer to a liquid which is constituted at least in part by water but may include other water-miscible liquids such as an alcohol (eg ethanol, isopropanol). In any event the skilled person will recognize that the aqueous liquid must be suitable for spray drying according to the methods of the invention.

The dry powder formulations of the present invention may be used for the treatment or prevention of diseases or conditions, depending on the biologically active peptides or proteins incorporated into the formulations. When the biologically active peptide or protein is an antigen the dry powder formulation may be used as a vaccine.

The biologically active agent may be any protein or peptide, or combination thereof. The present invention is specifically suited to formulations of the peptide, oxytocin, its derivatives (including analogues and agonists) as well as other similar agents such as vasopressin and desmopressin. Formulations containing oxytocin and/or its derivatives can be used in the treatment or prevention of postpartum hemorrhage (PPH). In such circumstances the formulation may also include other components suitable for treating or preventing PPI-1, such as ergometrine and related drugs. Formulations containing oxytocin and/or its derivatives may also be useful in treating anxiety and autism, as well as for inducing behavior modification. For example, psychiatric diseases or conditions including autism, schizophrenia, anxiety, stress and depression including post natal depression: cancer including breast, ovarian and endometrial carcinoma, as a life style drug involving trust, bonding and treating sexual dysfunction, in treatment of pain such as chronic headache, in lactation and in fertility, male or female.

The components used to form the amorphous glass matrix in the final spray dried powder can be any suitable mono, di- or polysaccharide and/or amino acid. For example, this component may comprise D-mannitol and glycine. These components will generally be dissolved in the water of the aqueous solution/suspension.

In another embodiment this component may comprise trehalose or inulin. A person skilled in the art would be well aware of saccharides and/or amino acids suitable for this purpose. Sugar alcohols may for example include xylitol and sorbitol. Monosaccharides may for example include but not limited to glucose (dextrose), fructose (levulose), galactose, xylose and ribose, and may include any combination of stereoisomers. Disaccharides may for example include but not limited to lactose, sucrose, trehalose, maltose. Alternatively it may include trisaccharide such as raffinose, tetrasaccharides such as stachyose, and pentasaccharides such as verbascose.

The micronized particles, optionally containing one or more other physiologically active agents, may further include one or more pharmaceutically acceptable carriers, diluents or excipients. Other excipients may include, but not be limited to, bulking agents, buffer agents and stabilisers such as sodium citrate, absorption enhancers, protease and peptidase inhibitors, taste or smell modifying agents, adhesion modifiers, flow agents, dissolution modifiers, or mucolytics.

The powders may additionally be formulated by combination with any known carrier particles, or other additives excipients such as flavour, smell or organoleptic sense modifiers. Some improvement may also be achieved by pelletising the powder into soil pellets with improved powder flow, and appropriate selection of dry powder inhaler accordingly.

The particles of the dry powder formulation typically have a mass median aerodynamic diameter of less than 10 microns, more preferably less than 5 μm and most preferably less than 3 μm. Preferably the L-leucine will represent between 5 and 50% by weight of the dry ingredients of the formulation. More preferably, the L-leucine will comprise between 10 and 40% by weight of the dry ingredients of the formulation.

As used herein the term "aerodynamic diameter" ($D_{ae}$) is defined as the diameter of an equivalent volume sphere of unit density with the same terminal settling velocity as the actual particle in question. Lung deposition of pharmaceutical powders is generally expressed in terms of particle's aerodynamic behaviour. Particles under the influence of gravity will settle to the ground at a certain velocity. In aerodynamic diameter, that velocity is assumed that it can be measured and takes into account the particle's unit density ($p_0$), particle density ($p_p$), unit density of a equivalent sphere ($D_{eq}$), Dynamic shape factor (X). For particles larger than about 1 μm the following equation applies to relate aerodynamic diameter and equivalent volume sphere of unit density.

$$D_{ae} = D_{eq}\sqrt{\left(\frac{\rho_p}{\rho_o X}\right)}$$

The term "mass median aerodynamic diameter" ("MMAD") is a statistical representation of the distribution of particle sizes graded according to aerodynamic diameter, defined herein as the median aerodynamic diameter expressed on a mass weighted basis, and is a widely accepted parameter used by aerosol scientists. The mass median aerodynamic diameter (MMAD) can be measured by a pharmacopeia impactor method as defined by the US Pharmacopeia, by using an Andersen cascade impactor, or by Next Generation Impactor (NGI). In this respect, in order for the dry powder to be highly aerosolisable, the particles will generally have a mass median aerodynamic diameter of less than 10 μm, but preferably less than 6 μm, preferably less than 5 μm, more preferably less than 3.5 μm or most preferably less than 2 μm.

The emitted dose (ED) is the total mass of the active agent emitted from the device following actuation. It does not include the material left on the internal or external surfaces of the device, or in the metering system including, for example, the capsule or blister. The ED is measured by collecting the total emitted mass from the device. It may be conducted in an apparatus frequently identified as a dose uniformity sampling apparatus (DUSA), and recovering this by a validated quantitative wet chemical assay (a gravimetric method is possible, but this is less precise). Alternatively, where an impactor or impinger is used, the ED is measured by combining the dose collected across all the stages of the respective impactor or impinger system.

The tine particle dose (FPD) is the total mass of active agent which is emitted from the device following actuation which is present in an aerodynamic particle size smaller than a defined limit. This limit is generally taken to be 5 μm if not expressly stated to be an alternative limit, such as 3 μm, 2 μm or 1 μm, etc. The FPD is measured using an impactor or impinger, such as a twin stage impinger (TSI), multi-stage impinger (MSI), Andersen Cascade Impactor (ACI) or a Next Generation Impactor (NCI). When using a TSI, the FPD is generally taken at 6.4 μm as this impinger has only one cut point which is estimated at this value. Each impactor or impinger has a pre-determined aerodynamic particle size collection cut points for each stage. The FPD value is then obtained by interpretation of the stage-by-stage active agent recovery quantified by a validated quantitative wet chemical assay (a gravimetric method is possible. but this is less precise) where either a simple stage cut is used to determine FPD or a more complex mathematical interpolation of the stage-by-stage deposition is used.

The fine particle fraction (FPF) is normally defined as the FPD divided by the ED and expressed as a percentage. Herein, the FPF of ED is referred to as FPF(ED) and is calculated as FPF(ED)=(FPD/ED)×100%.

The fine particle fraction (FPF) may also be defined as the FPD divided by the MD and expressed as a percentage.

The spray drying may be carried out using spray drying equipment well known to a person skilled in the art. It has now been found that the use of L-leucine in the solution for spray drying allows the spray drying to be achieved at temperatures lower than the temperatures generally required for this purpose. Since the temperatures used in the spray drying process can cause decomposition of the active agent this is a particular advantage of the present invention. For example, the spray drying of the solutions/suspensions of the present invention can be achieved at temperatures of less than 80° C., preferably less than 60° C., more preferably less and 40° C. and most preferably less than 30° C. or at ambient temperatures. Depending on the spray dryer configuration, these temperatures may refer to the dryer inlet temperature or outlet temperature, but preferably will refer to the temperature experienced by the drying droplets, which due to the evaporative cooling effect is often the outlet temperature of the system.

The dry powder prepared by the present invention is novel and presents a further aspect of the present invention. According to this aspect there is provided a dry powder formulation comprising:

a biologically active protein or peptide, an amorphous glass matrix comprising one or more mono, di- or polysaccharides and/or amino acids, and L-leucine.

In a preferred embodiment the amorphous glass matrix comprises D-mannitol and glycine, trehalose and/or inulin. Alternatively, it may comprise a polymer such as a dextran, or PVA or PVP, or any known glass forming material such as those known in freeze drying lyophilisation.

Particles of the dry powder formulation will have at least a portion of the L-leucine located at the surface. In a preferred embodiment the surface will comprise at least a 50% coverage by the L-leucine, more preferably more than 75% and most preferably more than 90%. Assessment of L-leucine presence at the surface may be measured directly using a technique such as ToFSIMS (Time of flight secondary ion mass spectrometry) or XPS (x-ray photoelectron spectroscopy). Alternatively it may be assessed by inverse phase gas chromatography. A preferred method to assess is the indirect approach outlined below via measurement of powder cohesion.

As mentioned above, it is believed that the concentration of L-leucine at the surface acts to protect the dry particles from agglomeration and the ingress of moisture.

The dry powders of the present invention can be administered using equipment and techniques known in the art. In this regard there are many inhalation devices described in the art for the purpose of allowing a patient to inhale a dry powder and this equipment may be used for the administration of the dry powders of the present invention.

Dry powder inhaler devices (DPIs) arc well known in the art and there are a variety of different types. Generally, the dry powder is stored within the device and is extracted from the place of storage upon actuation, of the device, whereupon the powder is expelled from the device in the form of a plume of powder which is to be inhaled by the subject. In most DPIs, the powder is stored in a unitary manner, for example in blisters or capsules containing a predetermined amount of the dry powder formulation.

Some DPIs have a powder reservoir and doses of the powder are measured out within the device. These reservoir devices may be less favoured where the treatment is likely to be one or a small number of doses in an isolated treatment Dry powder inhalers may be passive or active. Passive inhalers are those whereby the powdcr is aerosolised using the air Bow drawn through the device by the patients inwards breath, and active devices are those whereby the powder is aerosolised by a separate source of energy, which may for example be a source of compressed gas such as the Nektar Exubera device or Vectura Aspirar device, or a form of mechanical energy such as vibration (such as the Microdose device) or impact.

The dry powder inhaler devices suitable for use in the present invention include "single dose" devices, for example the Rotahaler (trade mark), the Spinhaler (trade mark) and the Diskhaler (trade mark) in which individual doses of the powder composition arc introduced into the device in, for example, single dose capsules or blisters. Devices may be presented as pre-metered for example with powder in a blister strip (as with the GSK Diskus device) where the pre-metered format comprises multiple doses) or where the patient inserts a pre-metered external dose form, such as a capsule containing the drug (for example the Boehringer Ingelheim Handihaler, or the Miat Monodose).

Alternatively, the device may be a reservoir device, where the powder dose is metered within the device from a powder reservoir during patient handling (for example the Astra Turbuhaler). Any of these inhaler device types may be used.

The device may preferably be a single use device, or one which is designed for use with a small number of doses, and may be disposable. For example, the Twincer device, the Direct Haler device, the TwinCaps device or the Puff-haler. An advantage of these devices is their simplicity, small number of components and low cost. Preferably a device with fewer than 10 independent components is preferred. More preferably, 5 or fewer, most preferably 3 or fewer.

There are a number of factors associated with the delivery devices which will affect the dosing efficiency achieved. Firstly, there is the extraction of the dose. Additionally, the dynamics of the powder plume generated will also affect dosing delivery. Preferably, the device will permit high emitted dose, and high efficiency de-agglomeration. High efficiency de-agglomeration is often associated with high levels of powder impaction on actuation. The device may have a low medium or high air flow resistance.

It should be appreciated, that the compositions of the present invention can be administered with either passive or active inhaler devices.

Delivery of biologically active protein and peptides in the pulmonary route using an inhalable dry powder formulation requires solubilising of the particles when they come into contact with the mucosal membrane of the lungs and subsequent release and uptake of the protein or peptide. While the L-leucine is believed to provide a form of hydrophobic coating to the spray dried particles sufficient to provide improved stability and shelf life, particularly in warm and humid environments, it has been surprisingly found that this does not interfere with the ability of the powders to release the proteins and peptides for uptake in the lung. Previously, it has been shown that coating particles with hydrophobic excipients can delay the dissolution for significant periods, as in WO 01/76575. In fact it has been found for a spray dried formulation comprising oxytoxin that the uptake of oxytoxin and time of onset of action is particularly rapid, and considerably faster than the current methods and formulation used to administer oxytoxin during childbirth. Accordingly, it has been surprisingly found that delivery of oxytoxin via inhalation into the lung provides significant advantages over current administration routes.

Accordingly, in a further aspect of the present invention there is provided a dry powder for inhalation comprising oxytoxin and/or a derivative thereof, and a pulmonary acceptable carrier, such as an amorphous glass matrix for the oxytoxin, wherein more than 40%, preferably more than 50%, more preferably more than 60% and most preferably more than 65% of the particles of the dry powder upon inhalation have an aerodynamic diameter of less than 5 μm, more preferably less than 3 μm. Preferably the mass median aerodynamic diameter (MMAD) of the aerosol cloud generated is less than 5 μm, more preferably less than 3 more preferably still less than 2.5 μm, and most preferably less than 2 μm.

The dry powder formulations according to this aspect of the invention are especially suitable for use in the treatment or prevention of post partum haemorrhage (PPH). The invention also provides the use of oxytocin and/or an oxytocin derivative in the manufacture of a dry powder for inhalation for the treatment or prevention of PPH. The invention also provides a method for the treatment or prevention of PPFI comprising administering to a subject in need thereof by inhalation an affective amount of a dry powder comprising oxytocin or an oxytocin derivative. Preferably the dry powder formulation is in a form described above.

In a preferred embodiment of this aspect of the invention the amorphous glass matrix comprises one or more mono-, di- or polysaccharides and/or amino acids, and most preferably the matrix will include L-leucine, preferably in amounts and proportions as described above. However, in other embodiments the amorphous glass matrix comprises an inert polymer suitable for pulmonary delivery, such as a polyvinylpyrollidone or polyvinyl alcohol or polyethylene glycol polymer or propylene glycol or co-polymers. Matrices composed of these polymers could also include components such as leucine, isoleucine or trileucine to improve the stability of the particles and to ensure they have an appropriate aerodynamic diameter.

According to this embodiment the dry powder may further include one or more other physiologically active agents, and further include one or more pharmaceutically acceptable and pulmonary acceptable components, such as those previously described. In a preferred embodiment the pulmonary acceptable carrier includes sodium citrate, or a stabilizer for the oxytocin component.

Micronized particles according to this aspect of the invention arc typically prepared by spray-drying as described above under suitable conditions which can be determined by the skilled person. The term "spray-drying" is intended to encompass any process in which a solution of one or more solutes or suspension is formed in a liquid, whereby the liquid is physically atomised into individual droplets which are then dried to form a dry particulate powder. It may encompass any form of a droplet to particle formation process, and may encompass related processes such as spray-freeze drying, spray chilling and spray flash drying. The droplets may be formed by any known atomisation process, including but not limited to pressure atomisation, pneumatic atomization, two or multiple fluid atomisation, rotary disc atomisation, electrohydrodynamic atomisation, ultrasonic atomisation, and any variant of such atomisation processes. The atomisation may occur from one spray source or multiple sources. The liquid vehicle spray may or may not be aqueous and may optionally comprise co-solvents plus additional components dissolved or suspended. The liquid may include a material that is a vapour or solid at ambient conditions but exists as a liquid under the selected process conditions. The droplets formed may be dried by applying heat in the form of a heated drying gas, or heat may be applied in other ways, for example radiatively from the walls of the drying chamber or as microwaves. Once collected from this drying process, the particles may be further dried or conditioned to a controlled moisture level via a process such as vacuum drying or freeze drying. Alternatively drying may be achieved by freezing followed by drying or by application of vacuum.

It will be recognised that any other means of obtaining such particles are also contemplated herein, for example super critical fluid synthesis, synthesis from emulsions and any other form of controlled precipitation that forms substantially spherical particles. Alternatively any forms of size reduction, attrition, milling and co-milling may be used to obtain suitably sized particles.

The particles may be obtained and engineered into any known particle engineering system, such as but not limited by the following: Pulmosphere™ or Pulmosol™ technology developed by Nektar, AIR™ porous particle technology develed by Alkermes, Technosphere™ technology developed by Mannkind, Powderhale™ technology developed by Vectura, particles created by Prosonix sonocrystalisation methods, particles created by wet or dry nano-milling technologies for example developed by Elan, Hovione or Savara.

The micronized particles of the dry powder for inhalation are of a size suitable for aerosolisation and inhalation, having a physical size less than 15 μm, such as less than 10 μm, or less than 6 μm, or less than 5 μm, or less than 3 μm or less than 2 μm. The particles according to this embodiment will have a mass median aerodynamic diameter of less than 10 μm, but preferably less than 5 μm, or less than 3 gm.

Typically, in addition to the size equivalents discussed above, 90% of the particles by volume may have an aerodynamic diameter of less than 10 μm, less than 8 μm, or less than 6 μm or less than 5 μm or less than 3 μm. The mass median aerodynamic diameter can be measured by a pharmacopeia impactor method as defined by the US Pharmacopeia, by using an Andersen cascade impactor, or by Next Generation Impactor (NGI). The particles according to this embodiment may have a mass median diameter of less than 5 μm, or less than 3 μm which could be measured by a laser light scattering method, such as using a Malvern Mastersizer 2000 instrument.

In order to obtain a high efficiency in aersolisation it is also advantageous for the particles to exhibit a low level of cohesion. Typically, cohesion may be measured using a powder shear cell test, such as the shear cell of the Freeman FT4 powder rheometer. Advantageously, a powder would exhibit a mean cohesion value of less than 2, more preferably less than 1.5 and most preferably less than 1.

In a further embodiment, respiratory delivery of oxytocin and/or its derivatives may also include nasal delivery. Nasal delivery involves inspiration via the nose but where the powder is primarily collected in the nasal cavity and turbinates, and where uptake into the systemic circulation also occurs. Nasal inhalation is similar to pulmonary administration as it provides a non-invasive route of delivery to the systemic circulation. Nasal delivery avoids needles and allows repeat administration from a single device.

Dose ranges can be readily calculated and administration without concern for liquid volume (not volume dependent). Delivery devices for powder nasal delivery may be different from those required for pulmonary delivery. Examples include devices from Optinose, the Via Nase (Kurve), the Direct-Haler, The Monopowder (Valois) or nasal powder systems from Bespack. The mass median particle size for nasal delivery is preferably in excess of 5 μm and more preferably greater than 10 μm as this reduces the material passing through the nasal cavity and maximises its deposition in the nasal turbinates. Nasal formulations will include nasally acceptable carrier and may include additional excipients such as bioadhesive polymers and penetration enhancers, for example chitosan, HPMC or carbopols. It is an especially preferred embodiment that oxytocin or one of it analogues or derivatives may be delivered as a formulated powder comprising a glassy matrix via the nose, in a mass median particle size greater than 10 μm for the treatment of PPH, or other related maternal conditions such as post natal depression, and preferably have a rapid onset of action. The dry powders prepared for pulmonary delivery may also be inhaled via the nasal passage into the pulmonary system, for example where a patient has difficulty inhaling the powder through the mouth, although this is not a preferred mode of delivery of such powders.

Oxytocin is the uterotonic agent of choice according to the World Health Organisation for use in the active management of third stage of labour, due to the speed onset of action, minimal side effect profile and the lack of contraindications. According to the clinical practice guidelines of The Royal Women's Hospital (Melbourne, Aus) prophylactic oxytocin should be administered to the woman with the birth of the anterior shoulder, or within one to two minutes of the birth of the baby. The timing of administration is critical in preventing uterine atony, and there is a clean benefit to providing a delivered form with the fastest onset following such birth to reduce the risk of ongoing blood loss.

In addition to the prevention of PPH, oxytocin is used as a treatment for PPH at a dosage of 30-40 IU in an intravenous infusion. In well controlled clinical settings low dose oxytocin (0.5-1 mU/ml, IV infusion) is indicated for the initiation or improvement of uterine contractions, where this is desirable and considered suitable for reasons of fetal or maternal concern, in order to achieve vaginal delivery.

More recently the scientific and medical literature has reported a link between low endogenous oxytocin levels and postnatal depression, and there may be an advantage in developing a practical, cost effective and non-invasive form of oxytocin on its therapeutically effective derivatives for systemic delivery in or around this area of indication.

In developing countries parenteral administration of oxytocin usage encounters a number of obstacles including the need for cold-chain storage to prevent chemical degradation, the need for trained medical personnel for administration of IV or IM injections, the potential for syringes to be reused in an effort to reduce costs which increases the likelihood of blood borne virus transmission and a general lack of access to high quality oxytocin products for the prevention and/or treatment of PPH. In an effort to increase access to oxytocin skill birth attendants in some countries are trained to administer IM injections of oxytocin, however there are numerous reports of inappropriate use of the parenteral product for labour augmentation. An inhaled oxytocin formulation would overcome many of the limitations associated with parenteral formulations. A single unit dosage form system would eliminate the potential for use in labour augmentation as it would not be possible to deliver the low dosage required. Providing oxytocin in an inhalable dry powder form also provides more flexibility with dosing in view of the absence of a liquid or gaseous carrier and the lack of volume dependency. It also avoids the need for needles, minimises the risk of contamination, and allows the flexibility for repeat administration from a single device.

The rapid onset of action achieved through the dry powder formulations of the present invention provides the ability to rapidly titrate the dosage during the treatment of PPH where the usual therapeutic dose is between 30-40 IU. Midwives/birth attendants will typically feel the uterus to assess when the magnitude of the contraction is sufficient for controlling PPH. The rapid absorption and onset of action (as demonstrated in a sheep model) indicates that it would be possible for multiple inhaled doses to be administered to achieve the necessary plasma levels required for effective uterine contractions. The wide therapeutic index of oxytocin is also beneficial for an inhaled therapy as variability in delivery efficiency or absorption would not cause serious side effects in patients.

According to the present invention the onset of action following inhalation of a dry powder comprising oxytocin and/or an oxytocin derivative into the pulmonary system, as measured by uterine contraction may be achieved within 200 seconds of inhalation, preferably within 150 seconds of inhalation, more preferably within 100 seconds of inhalation and most preferably within 60 seconds of inhalation. Preferably the time between pulmonary administration of a dry powder formulation according to the invention and onset of uterine contractions in comparison to the onset of action following I.M. injection of a solution of oxytocin and/or an oxytocin derivative is less than 80%, preferably less than 60% and most preferably less than 40% of the time between I.M. injection and onset of uterine contractions.

A wide range of peptides and proteins can be formulated according to the present invention. The present invention is particularly suitable for the administration of oxytocin or derivatives, and similar peptides such as vasopressin and desmopressin. Examples of oxytocin derivatives include desamino-oxytocin, those described in Endocrinologica Experimentalis Vol 14, p 151, 1980, and agonists of oxitocin, such as carbetocin which has similar uses to oxytocin, focussing on the control of bleeding after delivery. Other oxytocin derivatives include deamino-1-monocarba-(2-O-methyltyrosine)-oxytocin, syntometrine and atosiban [d(CUMOT)]. However, the invention may also be used to provide dry powder formulations of other proteins including insulin and vaccines such as an influenza vaccine. In the case of vaccines, the formulation may also require additional immunostimulatory components. Examples of proteins and peptides which may be formulated according to the present invention and delivered by the pulmonary route include cytokines, hormones, clotting factors, vaccines and monoclonal antibodies.

The following is a list of proteins which may be used as the active agent in the compositions and processes according to the present invention. Calcitonin, erythropoetin (EPO), Factor IX, granulocyte colony stimulating factor (G-CSF), granulocyte macrophage colony stimulating factor (GM-CSF), growth hormone, insulin type I, interferon alpha, interferon beta, interferon gamma, interleukin-2, luteinizing hormone releasing hormone (LHRH), somatostatin analog, vasopressin analog, follicle stimulating hormone (FSH), amylin, ciliary neurotrophic factor, growth hormone releasing factor (GRF), insulin-like growth factor, insulinotropin, interleukin-1 receptor antagonist, interleukin-3, interleukin-4, interleukin-6, macrophage colony stimulating factor (M-CSF), nerve growth factor, parathyroid hormone, somatostatin analog, thymosin alpha 1, IIb/IIIa inhibitor, alpha antitrypsin, relaxin, anti-RSV antibody, cystic fibrosis transmembrane regulator (CFTR), deoxyribonuclease (DNase), bactericidal/permeability increasing protein (BPI), anti-CMV antibody and interleukin-1 receptor.

The invention will now be described with reference to some specific examples and drawings. However, it is to be understood that the particularity of the following description is not to supercede the generality of the invention as hereinbefore described.

EXAMPLES

Example 1

Spray Drying

Spray drying is a one-step process that involves the formation of powders from a starting solution of the desired dissolved material. By definition, it is the transformation of feed from a fluid state into a dried form by spraying the liquid feed into a hot drying medium. Four keys stages in the spray drying process are: (i) atomisation of feed through the nozzle, (ii) spray-air contact between the liquid droplets and the drying gas, (iii) drying of particles via evaporation of liquid, and (iv) collection of the final powder.

Figure 1:
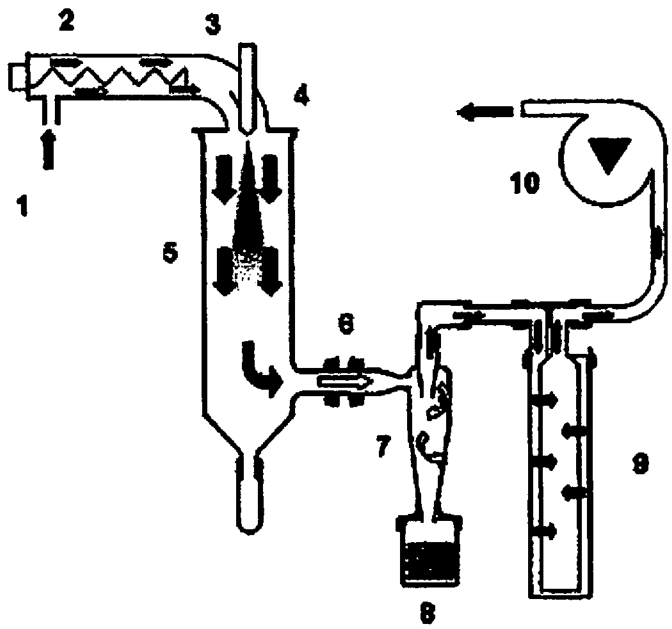
FIG. 1 is a schematic representation of an apparatus for spray drying.

Referring to the schematic in FIG. 1, the air is taken into the system 1 and heated by the supplied heater 2 prior to the measurement of the inlet temperature 3. The liquid teed is drawn up separately into the nozzle 4 where the droplets are formed and dispersed into the drying chamber 5 being mixed with the warm air. At this point, a dried particle is formed. The outlet temperature is measured 6 as the particles move into the cyclone 7 where the powder is separated from the air. The powder is trapped in the collection vessel 8 to be recovered whereas the air gets filtered from all the line particles that may have remained in the air stream at the bag filter 9. The circulation of air in the spray drying is continued by the work of the aspirator 10.

Atomisation is a very crucial part in defining the droplets, and hence the subsequent particle size and distribution. It involves forming a spray of droplets from the bulk liquid as the feed is pumped through to a small orifice in the nozzle. In the case of a two-fluid nozzle, the supplied gas impacts on the liquid bulk in the nozzle at high velocities. This high velocity gas creates high frictional forces over the liquid surfaces, causing the liquid to disintegrate and to form spray droplets, which project into the drying chamber.

The properties of the dissolved material and the drying conditions will influence the final powder characteristics. With evaporation of the liquid solvent from the droplet surface (water in this case) solute precipitation occurs. Often as the particle is forming, a crust may form and the crust may be porous, semi-porous or non porous allowing the removal of moisture at different rates and with varying effects. Particles of varying morphology can therefore form. Control of drying conditions is therefore an important consideration.

According to the experiments performed, formulations of the powders and their spray drying parameters were varied.

In all the powder formulations, mannitol was used as the baseline material, with varying amino acids added. The spray drying parameters that remained constant throughout were the aspirator setting, set at full flow and the atomiser airflow rate (800 L/hour).

For each formulation, the mannitol, glycine and oxytocin were spray dried at fixed amounts with varying amounts of leucine. The spray drying conditions were fixed with the outlet temperature set at 70° C.

The parameters that were used are shown in Table 1 below. The percentages shown of the amino acids were calculated to that of the mannitol amount only, not of the entire powder content. The percentage shown of oxytocin was that of the entire powder content.

TABLE 1

| Trial | 1 | 2 | 3 | 4 | 5 | 6 |
|---|---|---|---|---|---|---|
| Mannitol (g) | 5 | 5 | 5 | 5 | 5 | 5 |
| Glycine (%) | 30 | 30 | 30 | 30 | 30 | 30 |
| Oxytocin (%) | 1 | 1 | 1 | 1 | 1 | 1 |
| Leucine (%) | 15 | 50 | 15 | 50 | 32.5 | 32.5 |
| Liquid feed rate (mL/min) | 8 | 8 | 2 | 2 | 5 | 5 |

The powders were weighed out and dissolved in the appropriate amount of Milli-Q water to achieve the desired feed concentration. The solutions were then spray dried to produce dry powders using the Buchi 190 Mini Spray Drier (Buchi, Switzerland).

Example 2

In-Vitro Aerosol Deposition

Figure 2:
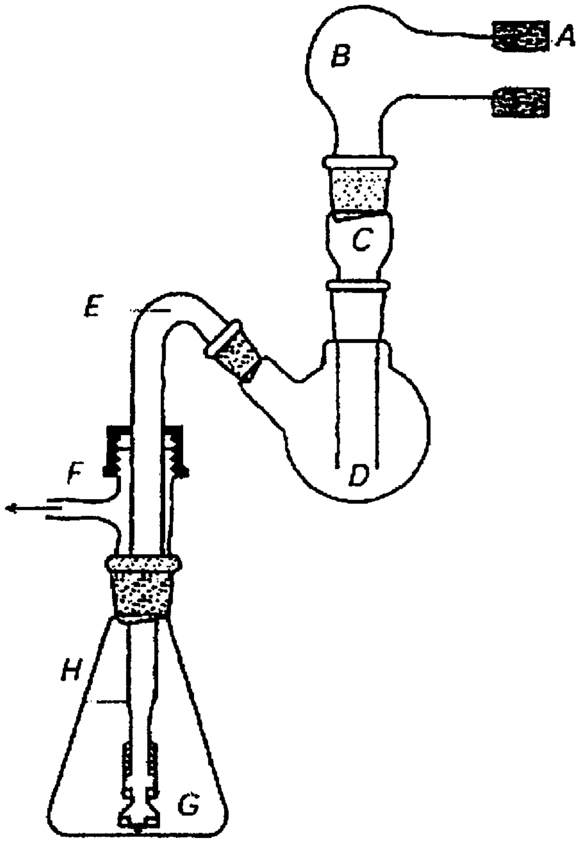
FIG. 2 is a schematic representation of a Twin Stage Impinger for measuring the in-vitro aerosol deposition of dry powders.

The in-vitro aerosol deposition of the powders was measured using the Twin Stage Impinger (TM) (Copley Scientific Ltd., Nottingham, UK). The TSI methods and set up was done so according to the British Pharmacopeia 2011 as shown in FIG. 2. In the glassware part D and part H, 7 mL and 30 mL of water respectively was added during the assembly of the TSI.

The TSI is a simple model of the respiratory tract; with the upper (stage 1) and lower (stage 2) chambers representing the upper and lower airways respectively. The cut off aerodynamic diameter at the first stage is 6.4 μm. Particles larger than 6.4 μm should ideally be collected in the 7 mL liquid; smaller particles (<6.4 μm) that are not collected will proceed to the lower stage, which contains 30 mL of liquid. Most particles will be collected in the lower stage due to the excess of liquid, however if particle size is too small for collection in the lower stage, they will be emitted at the exit.

Measurements for each powder sample were done in four replicates. For each replicate, five size 3 HPMC capsules were manually filled with 20.4±0.24 mg with the sample powder and placed in five Monodose inhalers (Miat, Italy). A vacuum pump was attached to part F and the airflow rate was calibrated to 60 L/min and was set to 5 seconds. The capsule was pierced in the device and placed on the adapter (pan A) ready to be activated by the vacuum pump. When the pump was turned on, the powder was carried from the inhalation device into the TSI apparatus.

All five capsules were activated into the same TSI. The used capsules and the inhalers were then washed with Milli-Q water into a 100 mL volumetric flask and made up to volume. This was called the 'residual' stage. The parts that made up Stage 1 (parts A, B, C and D) were washed into a 200 mL volumetric flask and the parts that made up Stage 2 (parts E, F, G and H) were washed into a 50 mL volumetric flask with Milli-Q water and called 'stage 1' and 'stage 2' respectively. The amounts of oxytocin in each stage of the TSI were determined by LC/MS assay. The fine particle fraction (FPF) was calculated as the amount of powder that had reached stage 2 of the TSI apparatus divided by total amount of drug that was assayed. This test was the most important measure as it can determine whether a powder containing oxytocin can be formulated with suitable aerosol deposition, and consequent absorption from the lung.

TABLE 2

| Trial Number | Fine Particle Fraction (%) |
|---|---|
| 1 | 57 |
| 2 | 70 |
| 3 | 67 |
| 4 | 73 |
| 5 | 64 |

Particles passing to the lower portion of the TSI device i.e. stage 2, were considered to be respirable, therefore the higher the fine particle fraction (FPF), the higher the chance of the drug reaching the alveoli and getting absorbed into the bloodstream, which is ideal in a DPI. The FPF of the five trials shown in Table 2 were high compared to an average FPF from traditional carrier formulation powders (~10-20%).

Results showed that the FPF could reach between 55 and 75% which means that very efficient levels of aerosolisation were achieved and high amounts of oxytocin in the formulations were delivered as the required therapeutically active dose.

Oxytocin Stability

Peptides can potentially be denatured due to extreme heat. From the tests that were conducted in this study, the only indication as to oxytocin stability was the LC/MS assay content following the TSI experiments. When oxytocin content was assayed from all the stages of the TSI apparatus, capsules and the inhalation devices, on average 90.23±5.41% of the initial capsule's dose was recovered, suggesting that oxytocin was not degraded from the temperatures used in the spray drying process or from the handling processes.

Example 3

Trehalose/Leucine

Trehalose is a non-reducing sugar with high glass transition temperature ($T_g$ of 117° C. that has been used as an excipient in various studies for stabilisation of protein in dry solid slate formulations. Sugar molecules are generally used as stabilising excipients in this context as they contain carboxyl groups that are able to form hydrogen bonds with the protein of interest and therefore stabilise the bio-macromolecule with hydrogen bond replacement in dry solid state. Spray-drying has been successfully used in various studies for the manufacturing of inhalable dry powder formulations as the process is able to produce line particles with particle size range that is suitable for pulmonary delivery.

In an attempt to formulate inhalable protein pharmaceuticals for pulmonary delivery, spray-dried trehalose is produced at relatively low outlet temperature of 70° C. in order to minimise the impact of heat stress on processing stability of the relevant protein. Conditions were otherwise the same as the examples described with mannitol and amino ac i ds.

Figure 3:
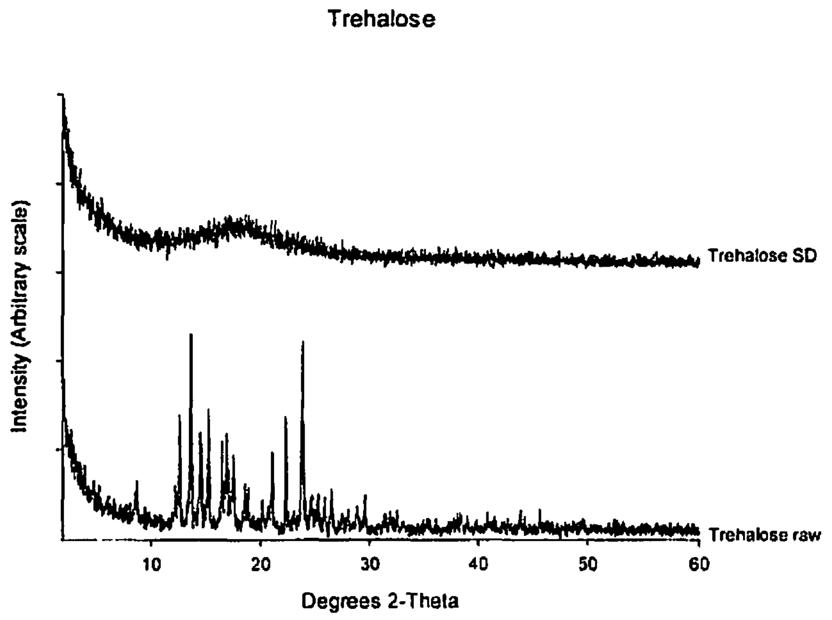
FIG. 3 provides X-ray diffractograms of raw trehalose Trehalose (raw) and spray-dried trehalose (SD) after spray-drying under specified conditions.

While trehalose is relatively crystalline as a raw material, spray-dried trehalose under the specified spray-dried conditions appears to be fully amorphous (see FIG. 3). This resultant formulation may further stabilise the protein of interest with glassy state stabilisation by providing an amorphous matrix which reduces molecular mobility of the bio-macromolecule in the formulation.

Figure 4:
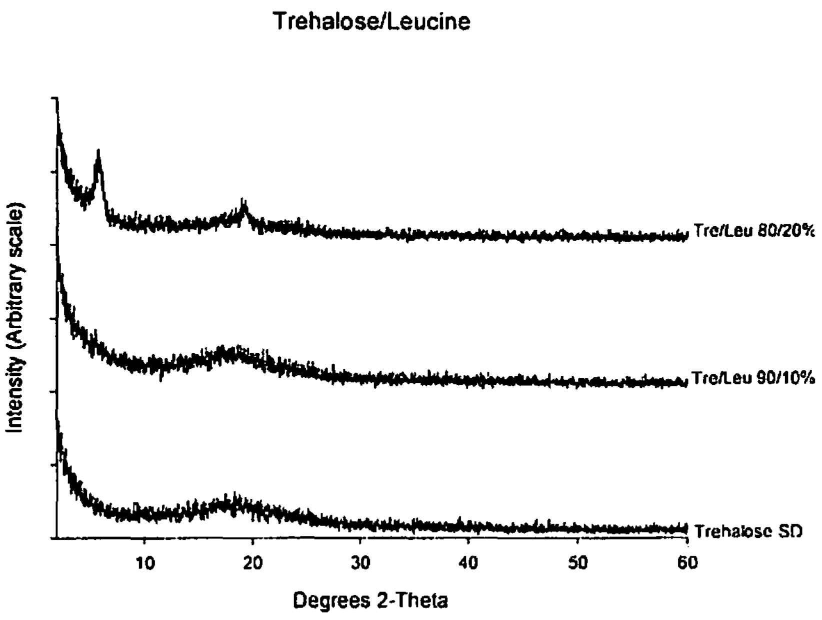
FIG. 4 provides X-ray diffractograms of spray-dried trehalose and spray-dried trehalose with leucine 10% and 20% w/w after spray-drying under the specified conditions.
Figure 5:
FIG. 5 is a scanning electronic microscope image of trehalose after spray-drying under specified conditions.
Figure 6A:
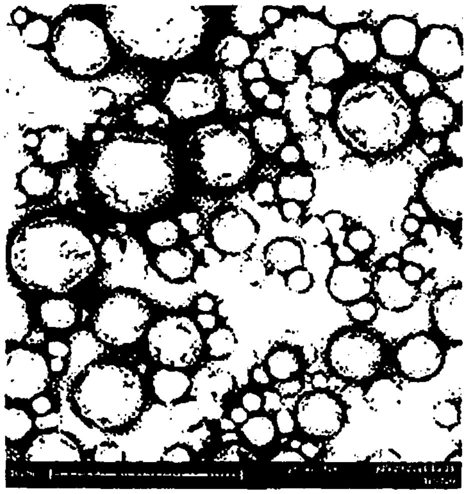
FIG. 6 provides scanning electronic microscope images of trehalose with leucine 10% w/w (left) and 20% w/w (right) after spray-drying under the specified condition.
Figure 6B:
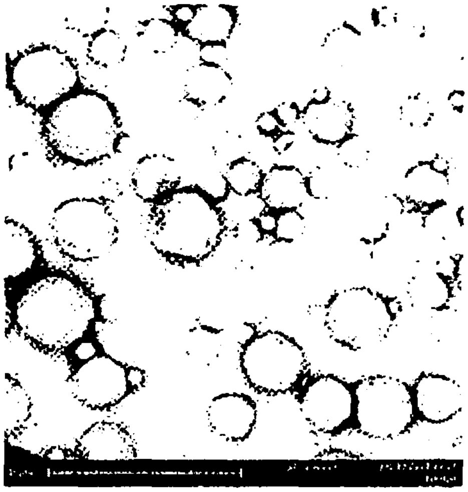

The resultant formulation of trehalose only is however, composed of fused primary structures with large particle size that is unlikely to be suitable for pulmonary delivery (FIG. 5). The incorporation of leucine in the formulation from a concentration of 10% w/w substantially improves particle size and morphology of the spray-dried formulation under the specified conditions (FIG. 6). The incorporation of leucine appears from this to be able to prevent fusion of the otherwise highly hygroscopic primary particle structures of trehalose from the spray drying process, and therefore retains the fine particle size range suitable for pulmonary delivery. In addition, the presence of leucine is also able to improve these particle properties over longer term storage, by providing a moisture protection of the internal amorphous matrix of the spray-dried trehalose formulations (FIG. 4).

Example 4

Materials

D-Mannitol was obtained from VWR International Ltd. (Poole, BH15 ITD, England). L-leucine (LEU), glycine (GLY) and L-alanine (ALA) were obtained from Sigma-Alrich Chemicals (Castle Hill, NSW, Australia).

Preparation of Spray-Dried Powders

Aqueous solutions containing mannitol and selected amino acids (LEU, GLY, ALA) in various compositions as shown in Table I were dissolved in 200 mL of Milli-Q water. A small amount of methylene blue (10 mg) was incorporated in each formulation to allow a simple quantification of powder by UV-VIS spectrophotometric analysis as described below. The prepared formulations were subsequently spray-dried using a Buchi 190 mini spray-dryer with a 0.5 mm two-fluid nozzle, using the following standard operating conditions: airflow rate, 800 L/h; pump setting, 5 (6.67 mL/min); aspirator setting, 20; outlet temperature, 75° C.

Particle Size Distribution Analysis

The particle size distribution of the powders was determined by laser-light scattering using the Malvern Mastersizer 2000 (Malvern Instruments Ltd, Worcestershire, UK) equipped with a Scirocco cell and a Scirocco 2000 dry powder dispersion unit. The powders were dispersed in air at a shear pressure of 3.0 to 4.0 bar, which was selected to achieve suitable de-agglomeration. The average particle size was measured in three replicates for each sample. The volume median diameter ($D_{50}$) was derived from the diffraction data using the in-built software for each sample.

In vitro powder aerosolisation and particle deposition

The in vitro powder aerosolisation performance and particle deposition was assessed using a twin stage impinger (TSI, Apparatus, A; British Pharmacopoeia, 2000) with the Monodose inhaler (Miat S.p.A., Milan, Italy) as the aerosol dispersion device. The flow rate was adjusted to 60 L/min using a Critical Flow Controller Model TPK 2000 & Flow meter model DFM 2000 (Copley Scientific Limited, Nottingham, UK). Approximately 20 mg of each powder was filled into size 3 1-IPMC capsules (Capsugel, Peapack, N.J., USA) for the tests which were performed at an air-conditioned laboratory (20±2° C., 50±5% relative humidity). Each capsule was actuated from the inhaler over 4 seconds for each measurement (n=5). The amount of powder deposited at different stages was determined using a UV-VIS light spectrophotometer as described below. The cut-off diameter for the TSI at 60 L/min is approximately 6.3 μm (Hallworth and Westmoreland. 1987).

The total amount of powder deposited in the inhaler, stage 1 ($S_1$) and stage 2 ($S_2$) was the recovered dose (RD). The amount of powder deposited in stage 1 and 2 was the emitted dose (ED) and it was calculated as the percentage of the RD (Eq. 1). The fine particle fraction (FPF) was defined as the percentage of RD deposited in stage 2 (Eq. 2).

$$ED\ \% = \frac{(S_1 + S_2) \times 100}{RD} \quad (1)$$

$$FPF\ \% = \frac{S_3 \times 100}{RD}. \quad (2)$$

Scanning-Electronic Microscopy (SEM)

The morphology of the particles was visualised under a scanning electron microscope (Phenom™, FEI company, USA). Powder samples were gently poured onto a double-sided carbon tape mounted on a sample holder for examination under the SEM. Excessive powder was removed to leave a fine layer of particles on the surface of the tape. The samples were sputter coated with gold using an electrical potential of 2.0 kV at 25 mA for 6 minutes with a sputter coater (K550X, EMITECH). SEM micrographs were captured using the in-built image capturing software.

Results

The volume median particle size ($D_{50}$) of all the formulations measured using Mastersizer 2000 are listed in Table 4. Spray drying mannitol alone produced small particles with $D_{50}$ of 1.87 μm. However, this powder was fully crystalline and did not have the amorphous glass structure required to stabilise bio-molecules.

Leucine is an excipient that can be used to improve aerosolisation of spray-dried particles, but also leucine assists in the formation of suitable small-sized particles. However glycine and alanine, though being structurally similar to leucine, were not able to achieve similar effects as they significantly increase the particle size of the formulations. It is worth noting that while initial concentration in feed solution is a known determinant of particle size, the range of solid loading used within the study design space did not appear to have a strong influence on geometric particle size as measured by laser diffraction. The total solid loading in the feed solution ranged from 2.50% to 3.72% in the present study. It is proposed that the change in particle size within this relatively small range of solid loading was negligible compared to the effects of the formulation excipients on cohesion and shape. Furthermore, considering the particle sizes produced from the mixed amino acids, it is possible that the combination use of these amino acids with leucine at appropriate concentrations may also influence particle size contrasting to that achieved by leucine alone.

Powder Dispersibility and De-Agglomeration

Spray-dried mannitol produced particles with $D_{50}$ of 2.83 μm which appears to indicate a satisfactory dispersibility for inhalable dry powder formulations, but it also produces the lowest emitted dose (ED). The retention of powder in the device after the experiment was visually evident, and suggests a more cohesive powder than other formulations here. The presence of amino acids in all combinations resulted in improved ED (Table 4). The beneficial effect of leucine was evident in its capacity to offset the effect of the other two amino acids on $D_{50}$ and of improving both de-agglomeration and ED.

In Vitro Aerosolisation and Particle Deposition

The TSI was used as a preliminary screen of this range of formulations to provide aerodynamic aerosol information.

Fine particle fraction (FPF) results show the formulations containing leucine, with $D_{50}$ below 5 μm demonstrate the highest FPF of greater than 68% (Table 4). Powders containing amino acids without leucine, with $D_{50}$ above 5 μm show significantly lower FPF as demonstrated by formulations containing glycine/alanine 30/30%, alanine 30% and glycine 30%, with FPF of 2.96%, 9.11% and 34.62%, respectively. While mannitol alone shows reasonable FPF of 66.20%, this formulation also demonstrates the lowest ED.). The combined amino acids at 15% were more effective at improving FPF (Table 4). These results suggest that the inclusion of glycine and alanine with leucine at the appropriate concentrations may improve formulation aerosolisation performance.

Surface Morphology

Spray-dried mannitol as a foundation material alone was observed to form small spherical particles that are heavily agglomerated. The result is consistent with the particle size distribution data from the Mastersizer. Upon addition of amino acids, spherical particles were preserved in all formulations containing leucine regardless of the presence of glycine and/or alanine. Other formulations containing glycine and/or alanine without the addition of leucine formed much larger particles of irregular shape with rough surfaces.

The result suggests that the presence of leucine assists in the formation of spherical particles by coating the drying particle surface, and therefore providing a protective shell which preserves the individual particles as they collect, preventing any fusion, while the presence of glycine and alanine did not prevent this effect. Previous results indicated that a relatively high concentration of leucine (i.e. >5% w/w) tends to lead to corrugated particles. The morphology of leucine-containing particles in the present study appears to behave differently. The concentrations of leucine used within the study design space (15 to 30 molar %), which corresponds to roughly 10 to 18% w/w, did not form corrugated particles. It is therefore speculated that the presence of glycine and/or alanine altered the core structure of the spherical drying particles, while leucine tended to reside on the particle surface, providing a coating to reduce surface cohesiveness and prevent fusion in the drying process.

In the present study, leucine was able to enhance aerosolisation performance of the mannitol formulations without necessitating the formation of corrugated particles. Furthermore, the FPF results suggest that this may be advantageous.

TABLE 3

| Factors | Levels of factors used in the formulation −1 | 0 | +1 |
|---|---|---|---|
| $X_1$ = leucine (molar %) | 0 | 15 | 30 |
| $X_2$ = glycine (molar %) | 0 | 15 | 30 |
| $X_3$ = alanine (molar %) | 0 | 15 | 30 |

| Responses | Process and formulation parameters kept constant |
|---|---|
| $Y_1$ = Mastersizer $D_{50}$ (μm) | Mannitol content: 5 g |
| $Y_2$ = Spraytec $D_{50}$ (μm) | Feed solution volume: 200 mL |
| $Y_3$ = Spraytec ED (mg) | Aspirator setting: 20 |

TABLE 3-continued

| | |
|---|---|
| $Y_4$ = TSI fine particle fraction (%) | Pump setting: 5 (6.67 mL/min) |
| $Y_5$ = TSI ED (%) | Airflow: 800 L/h |
| $Y_6$ = cohesion value (kPa) | Outlet temperature: 75° C. |

Abbreviation: ED, emitted dose; SD, spray-drying; TSI, twing-stage impinger.

TABLE 4

| Batch | $X_1$ | $X_2$ | $X_3$ | $Y_1$ | $Y_2$ | $Y_3$ | $Y_4$ | $Y_5$ | $Y_6$ |
|---|---|---|---|---|---|---|---|---|---|
| 1 | 0 | 0 | 0 | 1.87 | 2.83 | 15.80 | 66.20 | 78.04 | 4.53 |
| 2 | 30 | 0 | 0 | 1.75 | 2.70 | 17.50 | 80.10 | 91.11 | 2.21 |
| 3 | 0 | 30 | 0 | 3.75 | 5.52 | 19.20 | 34.62 | 89.59 | 2.39 |
| 4 | 30 | 30 | 0 | 2.05 | 3.50 | 18.00 | 72.62 | 88.00 | 1.04 |
| 5 | 0 | 0 | 30 | 6.69 | 12.02 | 18.90 | 9.11 | 92.17 | 0.71 |
| 6 | 30 | 0 | 30 | 2.27 | 3.24 | 17.50 | 68.64 | 89.99 | 1.21 |
| 7 | 0 | 30 | 30 | 13.97 | 28.55 | 19.20 | 2.96 | 85.90 | 0.43 |
| 8 | 30 | 30 | 30 | 1.97 | 3.58 | 17.20 | 69.13 | 87.40 | 1.32 |
| 9[a] | 15 | 15 | 15 | 2.05 | 2.58 | 16.60 | 76.84 | 88.79 | 1.82 |
| 10[a] | 15 | 15 | 15 | 1.95 | 2.49 | 17.40 | 76.40 | 86.97 | 1.79 |
| 11[a] | 15 | 15 | 15 | 1.99 | 2.28 | 16.40 | 74.27 | 88.82 | 2.11 |
| 12[a] | 15 | 15 | 15 | n/a | 2.40 | 17.0 | n/a | n/a | 1.32 |

[a]Indicates the centre point of the design.
Abbreviation: n/a, not available.

Example 5

In Vivo Testing

On day 135 gestational age, pregnant ewes (n=5) were anaesthetised with thiopentone in preparation for surgery. Isuflorane (2.5% in oxygen) was used to maintain anaesthesia and depomycin, procaine penicillin and dihydrostreptomycin were given for pain relief and to reduce the risk of infection. Each ewe was shaved and a 10 cm incision was made in the abdominal skin at the midline below the navel to expose the uterine wall, with care taken to avoid large blood vessels.

Three sterile stainless steel wires for measuring electromyographical (EMG) activity (0.07 mm diameter, inside a 2 mm catheter) were embedded in the smooth muscle layer of the myometrium surrounding the womb and held there by two stitches. The electrodes were passed through a catheter and out of the ewe via a small incision (2 cm) through the right flank. A catheter was inserted in the right jugular to allow for blood samples and to induce labour. Ewes were returned to metabolic cages and given 3-5 days to recover from surgery.

Labour was induced with two 5 ml intravenous injections of dexamethasone (consisting of 5 mg of dexamethasone phosphate and 10 mg of dexamethasone phenylpropionate) 24 hours apart. Labour occurred 54±2 hours after the first dexamethasone injection.

Oxytocin administrations, as detailed above, were performed within 15 hours of delivery. Each sheep received an intra-tracheal dose of dry powder oxytocin formulation, an intra-tracheal instillation of oxytocin in solution and an intramuscular injection of oxytocin. There was at least a one and a half hour washout period between each treatment.

For intra-tracheal administration, an endoscope was passed through the nasal passage into the trachea and positioned near the first bronchial bifurcation, where either a 1 mL aliquot of oxytocin in solution (10 IU) was released or 10 mg (average) of dry powder was delivered through a modified PennCentury powder delivery device.

The dry powder formulation comprised a spray dried composition, as described in example 1. This powder contained 13 units of oxytocin per mg by mass, co-spray dried with equal proportions by mass of mannitol, glycine and leucine.

Figure 9A:
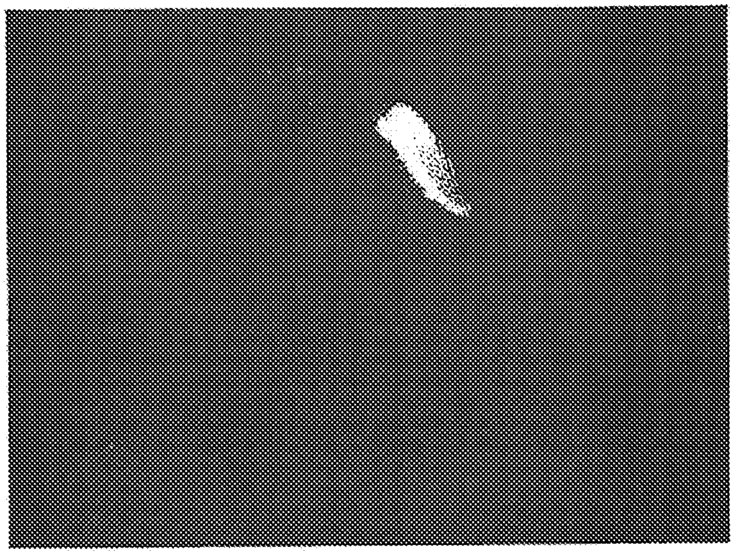
FIG. 9 shows bronchoscope video images of a sheep trachea before (a) and after (b) powder delivery.
Figure 9B:

During this procedure, bronchoscope video images were captured using a Linvatec IM3301 Pal Video Camera attached to an endoscope (Pentax FG-16X), which was saved as a digital file onto a computer using Video Capture Software. Examples of the images are provided in FIGS. 9*a* and 9*b*. The image in FIG. 9*a* shows the sheep trachea before powder delivery, and the FIG. 9*b* shows the image approximately 30 seconds from delivery. FIG. 9*b* shows clear evidence of white undissolved powder, as white patches not present before delivery, indicating that immediate dissolution had not occurred within the pulmonary system.

Figure 7:
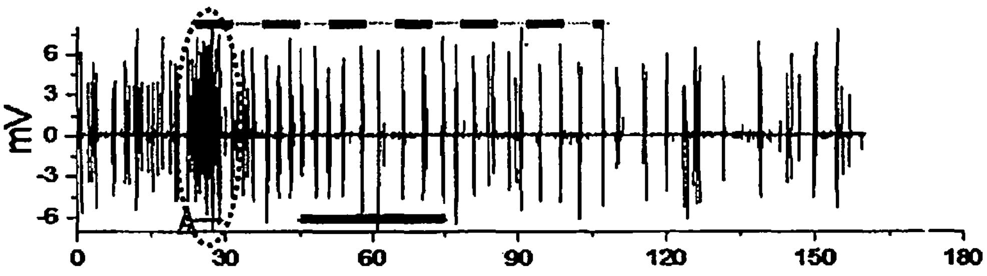
FIG. 7 is an EMG trade showing uterine contraction following inhalation of oxytocin. The arrow denotes the delay between administration and contraction. The initial burst is circled with a dotted line. The black line represents a random thirty minute sample of oxytocin induced activity. The dashed line represents the total time oxytocin induced uterine activity lasted before returning to baseline.

A cyberamp 380 in conjunction with MACLAB hardware (400 Hz Sample rate) and Chart 4 software (10V Input range) was used to display and record action potential originating from smooth muscle cells within the uterus. The cyberamp 380 used the AI401probe with positive input set at AC and negative input set at Ground. The AC cut off was 10 Hz and the prefilter gain set at 100 mV. The low pass filter was set at 300 Hz, the notch filter set to off, the output gain set to 5 and the total gain left at 500. Two way repeated measure ANOVA was performed to determine the statistical significance of our data. See FIG. 7.

Figures 8A, 8B, 8C, 8D:
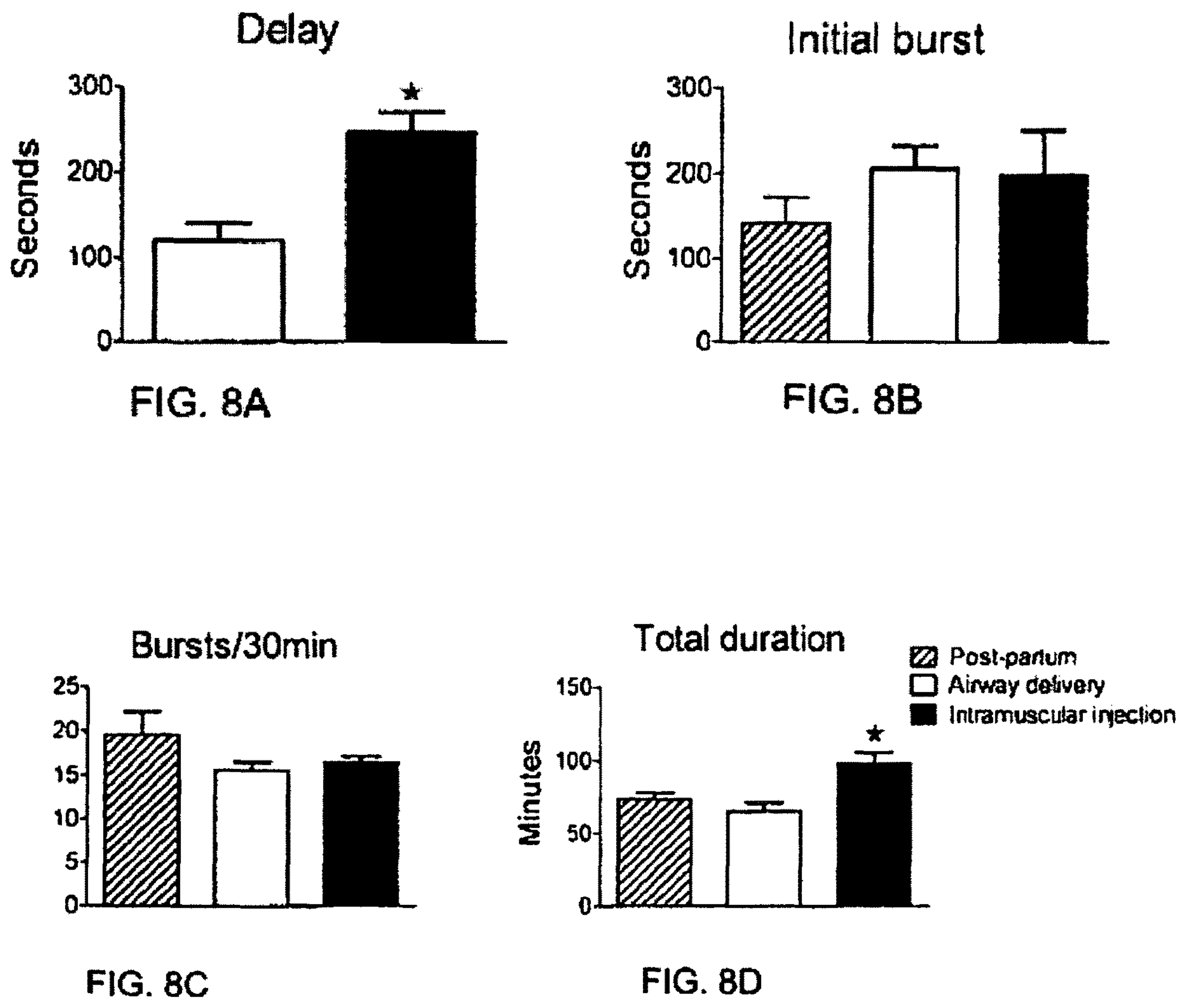
FIG. 8 is a series of charts providing an analysis of Uterine EMG behaviour during the immediate post-partum period and following intrapulmonary (IP) and intramuscular (IM) oxytocin delivery. (a) Delay between oxytocin administration and EMU response; (b) Length of the first EMG burst; (c) Number of EMG burst in the first 30 minutes; (d) Total duration of EMG activity. Data expressed as mean±SEM, P>0.05 RM ANOVA; n=5. Green bars represent uterine activity immediately after delivery, blue bars represent uterine activity after dry powder delivery and red bars represent uterine activity after intramuscular administration.

A number of properties of recorded EMG activity were analysed. With regard to elapsed time (delay) from delivery of oxytocin to the initial burst of EMG activity, delivery via the lungs results in a faster time of onset for the first contraction in contrast to IM delivery (FIG. 8*a*). No differences were seen in the length of the initial burst of EMG activity (FIG. 8*b*) nor was there a difference in the number of bursts occurred over the first 30 minutes following the initial burst of activity (FIG. 8). However, the total duration of EMG activity was significantly longer for IM of oxytocin compared to airway delivery and the normal activity observed immediately post-partum (FIG. 8).

These in vivo studies demonstrate that uterine contractile responses to oxytocin administered via pulmonary delivery occur on average after approximately 120 seconds in contrast to the IM delivery which occurred on average after approximately 250 seconds. Surprisingly, the onset of action from the powder pulmonary delivery was significantly more rapid compared to intramuscular delivery, and was also consistent with the plasma versus time profiles. The average onset of action was approximately 50% less than for IM. This is despite the fact that the dry powder particles contain approximately 30% leucine which is a poorly soluble and hydrophobic amino acid, which could be expected to delay dissolution. Furthermore, it is expected that a substantial proportion of the leucine will be present at the surface of the powder. The image 9*b* supports this concept that rapid dissolution of such powder is not expected in this environment. The data also demonstrates that uterine contractile responses to pulmonary dry powder oxytocin mimics the activity seen naturally in the immediate post-partum period, as observed with the length of the initial burst of uterine activity and the total number of EMG activity bursts recorded over the following thirty minutes.

Example 6

Dry Powder Influenza Antigen Formulation

The powder sample of influenza antigen, haemagglutinin (HA), was first dissolved with other excipients (i.e. mannitol 45% w/w, glycine 45% w/w and leucine 10% w/w) into an aqueous solution to produce a final formulation with an antigen loading of 5 μg HA per mg of powder. This solution was then spray-dried in a Buchi 190 laboratory spray dryer, at a relatively low temperature i.e. 70 degrees C. outlet temperature to minimise the effect of heat stress on the integrity of the antigen at the following spray-drying conditions: pump setting 6.7 mL/min; aspirator, 20 (100%); airflow, 800 l/hr. The spray-dried influenza antigen formulation was then collected from the collecting vessel for storage.

Example 7

Method for Testing Biological Activity of the Dry Powder Influenza Antigen Formulation The following describes the method for the testing of biological activity of the spray dried dry powder influenza antigen formulation containing haemagglutinin (HA) as the active protein. The haemagglutination assay (HA assay) is used to test the integrity of the HA protein in the dry powder formulation. The dry powder influenza antigen formulation of interest is first reconstituted with phosphate buffered saline (PBS) immediately before the test into a solution of standard HA protein concentration. A small amount of this reconstituted solution is then place into the first column of a 96-well plate. The solution is then diluted 1:2 with PBS across the 96-well plate by serial dilution. A standard amount of chicken red blood cell solution with a standard red blood cell concentration (i.e. 1%) is then added to each well of the plate. The plate is incubated at room temperature for 30 minutes immediately after addition of the red blood cells. Since intact HA protein will cause haemagglutination of red blood cells, the level of dilution that the HA containing solution is able to sustain before it is no longer capable of causing haemagglutination at 30 minutes will indicate the amount of intact HA protein in the formulation. The antigen was found to be in excess or 95% active, within the limits of this procedure.

Example 8

Cohesion Measurement of Particles and Preferred Cohesion Values.

Apparatus and Materials

The apparatus used were the 1 mL shear cell module, and vented piston, as part of the FT4 FREEMAN Rheometer unit (Freeman Technology, UK) and computer user interface and 1 mL shear cell conditioning module. The materials used were spray dried powders of 1:99% w/w_leucine/mannitol, 3:97% w/w_leucine/mannitol, 5:95% w/w_leucine/mannitol, and 10:90% w/w_leu/mannitol. These powders were produced following conditions of Example 1 above.

A powder sample was loaded into the cell and conditioned. During conditioning the 1 mL shear cell conditioning module was employed to gently disturb the powder as it moved throughout the whole sample. The purpose of this was to homogenise the powder by removing excess air and isolated pre-compacted powder particles. After conditioning, the powder was compressed. This was executed by the flat-surface vented piston in order to ensure uniform particle-particle interactions. Compression was followed by shearing. During shearing, a 24 mm shear cell (a unit component of: base, slide, splitting shim and shear cell module) was employed. The shear head comprising 18 blades, moved vertically downwards inducing normal shear stress while the shear head blades pierced the powder surface. The shear stress was then measured and was at maximum when the powder failed to resist the shear stress.

The graph of shear stress against normal stress was generated by the FT4 FREEMAN integrated software. From the graph, the extrapolated y-intercept provides the cohesiveness of the powder at zero consolidation. The ffc [the ratio of the major principal stress (consolidation stress), σ1, to the unconfined yield strength, σ1 data was also recorded.

TABLE 5

| Sample | Mean Cohesion (kPa) | Flowability (ffc) |
|---|---|---|
| 1% Leucine | 3.4 | 1.4 |
| 3% Leucine | 2.4 | 2 |
| 5% Leucine | 2.3 | 2 |
| 10% Leucine | 1.4 | 2.9 |

From 1 to 10% leucine content, an increase in leucine content decreases cohesion and improves flowability parameter (ffc).

This experiment was than repeated using spray dried leucine and PV1), produced and tested under similar conditions. The results were as follows:

TABLE 6

| Sample | Mean Cohesion (kPa) |
|---|---|
| 0% Leucine | 4.0 |
| 2% Leucine | 3.5 |
| 4% Leucine | 3.4 |
| 8% Leucine | 1.2 |
| 10% Leucine | 1.2 |
| 20% Leucine | 0.7 |

Example 9

Surface Energy Measurements

Samples

Two batches of powder were spray dried from water using the conditions as described in example 1, but where the powders comprised compositions of pure mannitol or mannitol with 10% w/w L-Leucine added.

Surface Energy Determination by Inverse Gas Chromatography

Surface energies of these powders were determined using Inverse Gas Chromatography (IGC, Surface Measurement Systems Ltd, and London, UK). Approximately 0.33 g of each powder was packed into prc-silanised glass columns (300 mm×3 mm internal diameter) which were loosely stoppered with silanised glass wool in both ends. The powder filled columns were conditioned for 2 h at 303 K before each measurement in order to remove impurities of surface. Probes were carried into the column by helium with a gas flow rate of 10 sccm (standard cubic centimetre per minute) and the retention times were detected by a flame ionization detector. The dead volume was calculated based on the elution time of methane which was run at a concentration of 0.1 $p/p^0$ (where p denotes the partial pressure and $p^0$ the vapour pressure).

Surface Energy Determination at Infinite Dilution:

GC grade hexane, heptane, octane, nonane and decane (all from Sigma-Aldrich GmbH, Steinheim, Germany) for non-polar surface energy ($\gamma^{NP}$), and two polar probes (i.e., dichloromethane and ethyl acetate) for polar surface energy ($\gamma^P$) were used at a concentration of 0.03 $p/p^0$. The detailed of $\gamma^P$ calculation was described elsewhere (Thielmann et al., Investigation of the acid-base properties of an MCM-supported ruthenium oxide catalyst by inverse gas chromatography and dynamic vapour sorption. Jackson, S. D., Hargreaves, J. S. J., Lennon, D., editors. *Catalysis in application* Great Britain, Royal Soc. Chem., p 237 (2003), and Traini et al., Drug Development and Industrial Pharmacy 34: 992-1001 (2008). FIG. 1 shows the surface energy contributions at infinite dilution:

The total surface energy ($\gamma^T$) was the additive result of non-polar ($\gamma^{NP}$) and polar contributions ($\gamma^P$) (Grimsey et al., *Journal of Pharmaceutical Sciences* 91: 571-583 (2002). The work of cohesion ($W_{co}$) was calculated (see Vanoss et al., *Langmuir* 4: 884-891 (1988) and Tay, et al., *International Journal of Pharmaceutics* (*Kidlington*) 383: 62-69 (2010). These experiments were run in triplicate.

Figure 10:
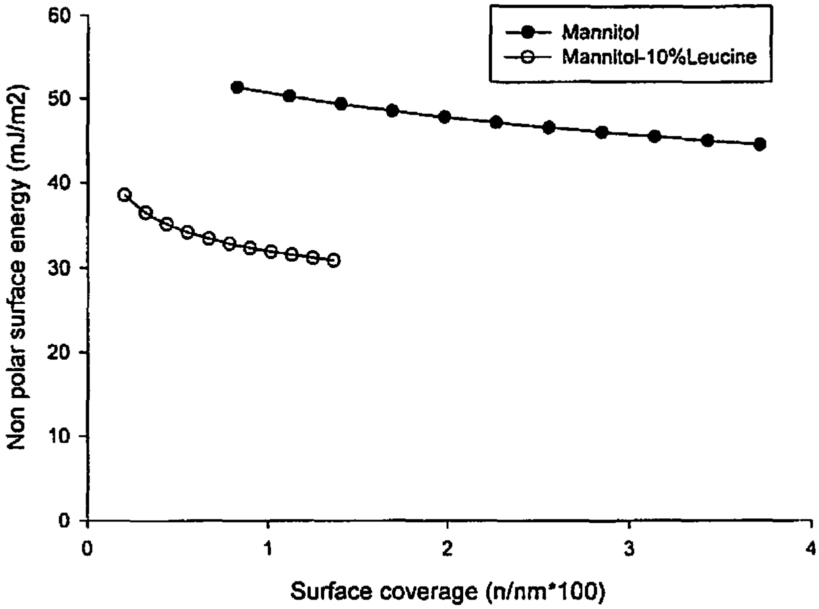
FIG. 10 shows non-polar surface energy distributions at finite dilution in Inverse gas chromatography.
Figure 11:
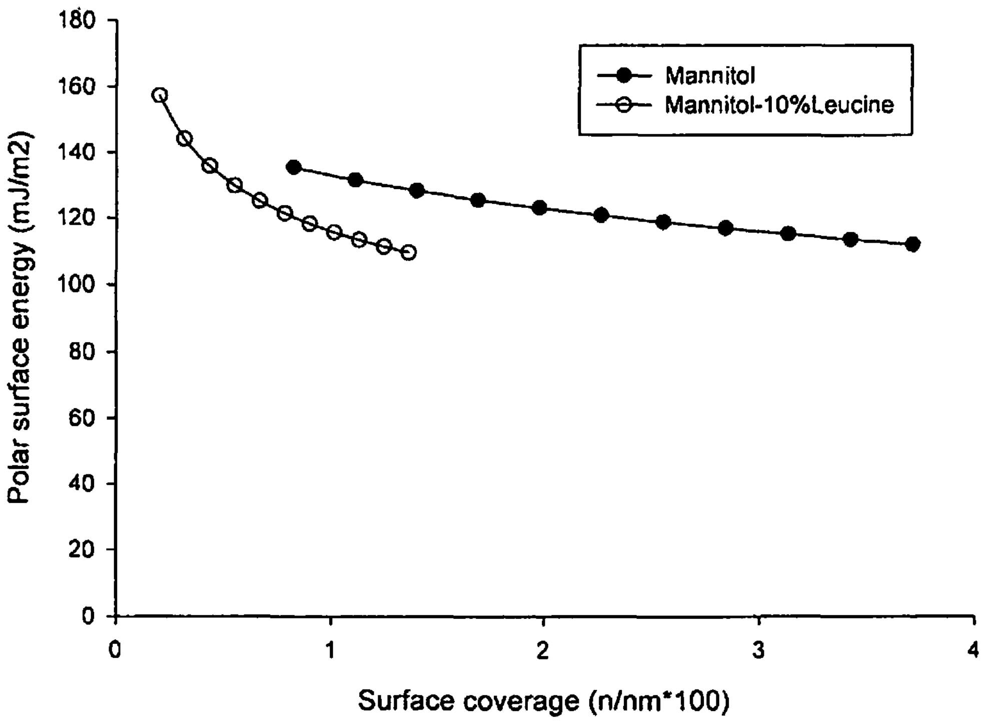
FIG. 11 shows polar surface energy distributions at finite dilution in Inverse gas chromatography.

Surface Energy Distributions and Surface Area Determination at Finite Dilution:

The distribution profiles of non-polar surface energy ($\gamma^{NP}$ profile) were determined according to the method described elsewhere (F. Thielmann et al, *Drug Development and Industrial Pharmacy* 33: 1240-1253 (2007) and Yla-Maihaniemi, et al., *Langmuir* 24: 9551-9557 (2008)). This is shown in FIG. 10. The non-polar surface energies at all coverages are clearly reduced for the leucine containing powder, and in this case shows a reduction by more than 30% at a 1% coverage level. The polar surface energy distribution is shown in FIG. 11.

The Brunauer-Emmet-Teller (BET) surface area was calculated from hexane adsorption isotherms. Dividing the adsorbed amount (n) by the monolayer capacity ($n_m$, the number of moles of the probe adsorbed for monolayer coverage), the surface coverage ($n/n_m$) was calculated. At each surface coverage, the net retention volume ($V_N$) was calculated for each probe. The non-polar surface energy ($\gamma^{NP}$) was calculated from the slope ($2 N_A \sqrt{\gamma^{NP}}$) of a plot of $RT1nV_N$ against a $\sqrt{\gamma^{NP}}$ of alkanes. The $\gamma^P$ and $\gamma^T$ were calculated at each surface coverage and their distribution profiles were then constructed (as described in Das et al. *Langmuir* 27: 521-523 (2011a)).

Figure 12:
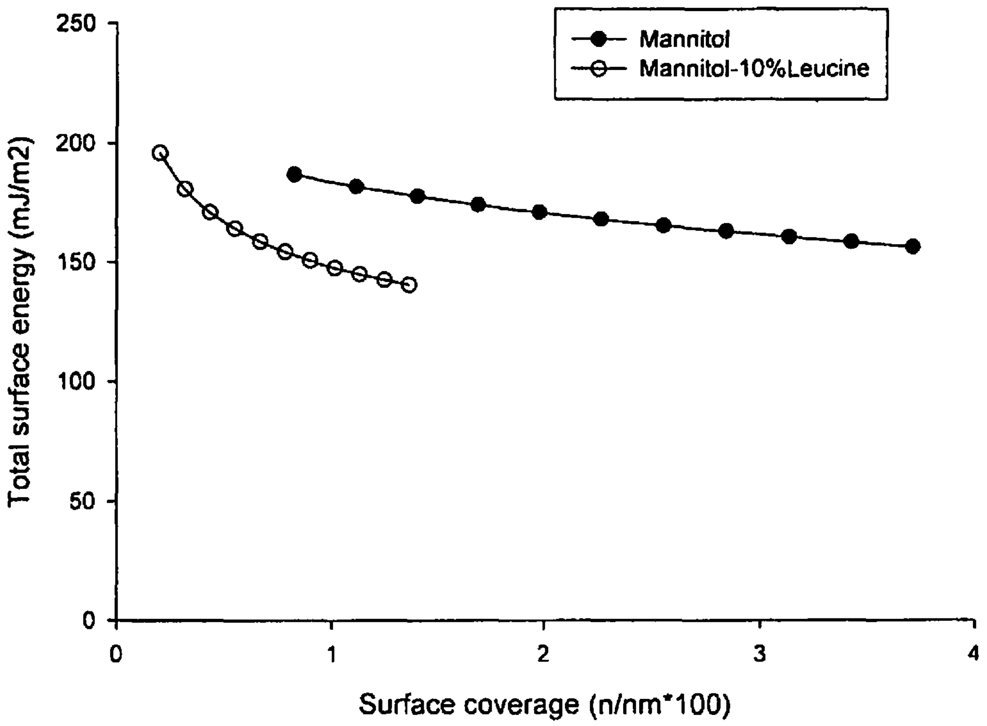
FIG. 12 shows total surface energy distributions at finite dilution in Inverse gas chromatography.
Figure 13:
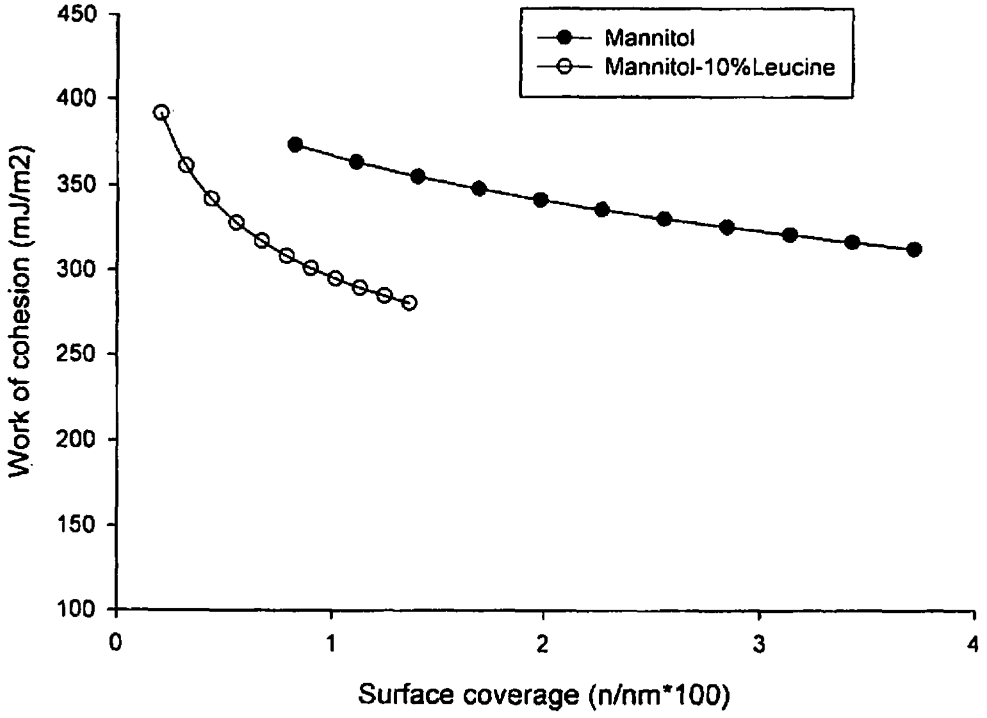
FIG. 13 shows work of cohesion surface energy distributions determined at finite dilution in Inverse gas chromatography.
Figure 14:
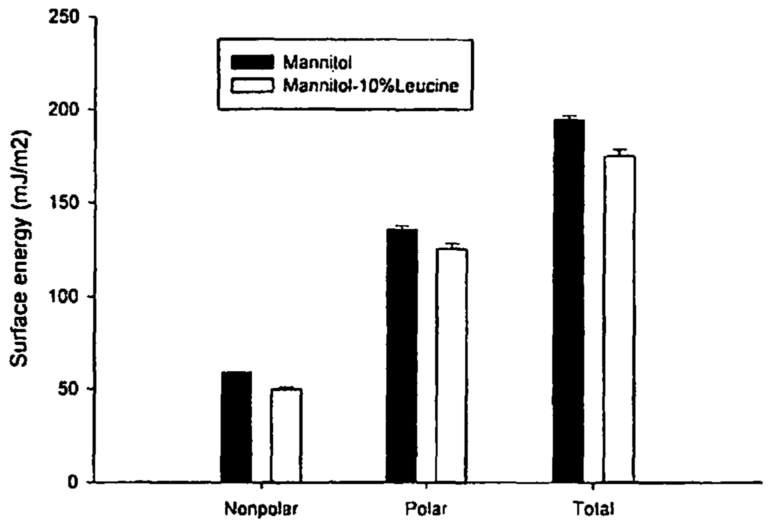
FIG. 14 shows surface energy at infinite dilution in Inverse gas chromatography.

FIGS. 12 and 13 show that the calculated total surface energy distributions and the work of cohesion are also substantially reduced in the case where leucine is added, for example by 20% or more at a surface coverage of approximately 1%.

Example 10

In Vivo Testing of Other Formulations

As per example 5 a single pregnant ewe was prepared by surgery to implant the EMG electrodes and a catheter to allow for blood collection. The induction of labour commenced on the same day as surgery also as per the method set out in example 5. Labour and delivery occurred 2 days after the beginning of the induction period.

Oxytocin administrations, as detailed below, were begun within 22 hours of delivery. There was a one and a half hour washout period between each treatment.

For intra-tracheal administration, an endoscope was passed through the nasal passage into the trachea and positioned near the first bronchial bifurcation, where a dose of dry powder (as detailed below) was delivered through a modified PennCentury powder delivery device. In addition to the dry powder delivery to the lung an intramuscular injection of oxytocin (as per example 5) was also delivered.

Figure 15A:
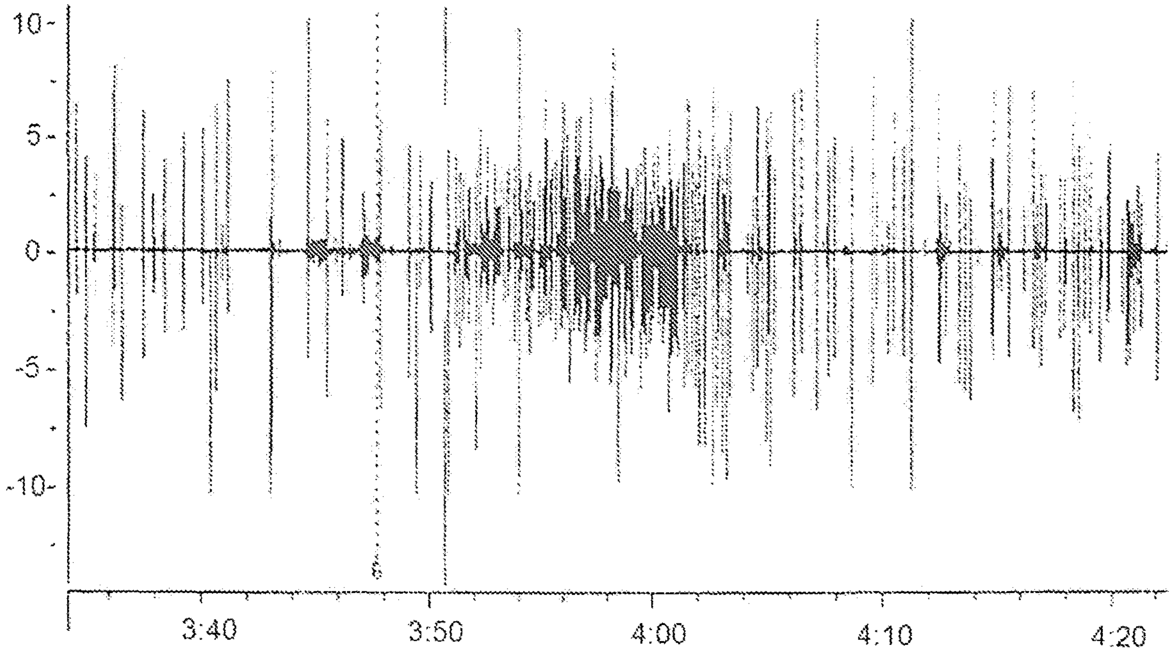
FIG. 15*a* is an EMG trace showing uterine contraction following inhalation of oxytocin delivered by example 10 formulation 1 containing mannitol; glycine and leucine in equal amounts. The dashed line shows the time of formulation delivery and the solid line the onset of uterine contraction. The x-axis is in hh:mm:ss and they axis is in mV.
Figure 15B:
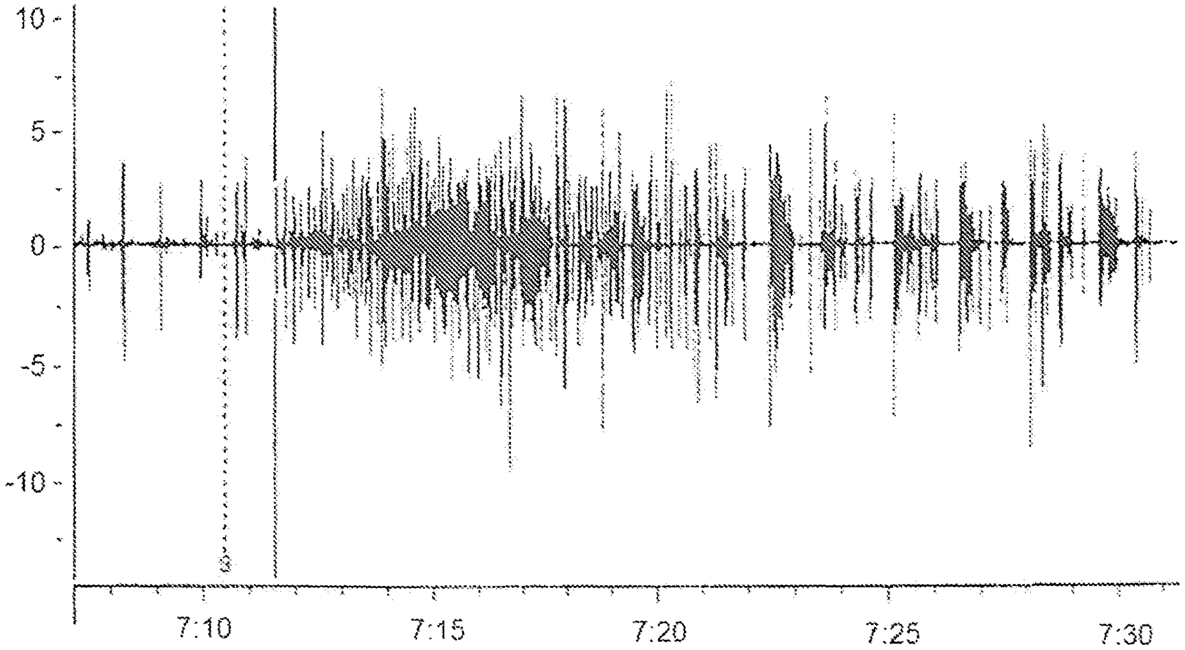
FIG. 15*b* is an EMG trace showing uterine contraction following inhalation of oxytocin delivered by example 10 formulation 2 containing 90% trehalose and 10% leucine. The dashed line shows the time of formulation delivery and the solid line the onset of uterine contraction. The x-axis is in hh:mm:ss and the y axis is in mV.
Figure 16A:
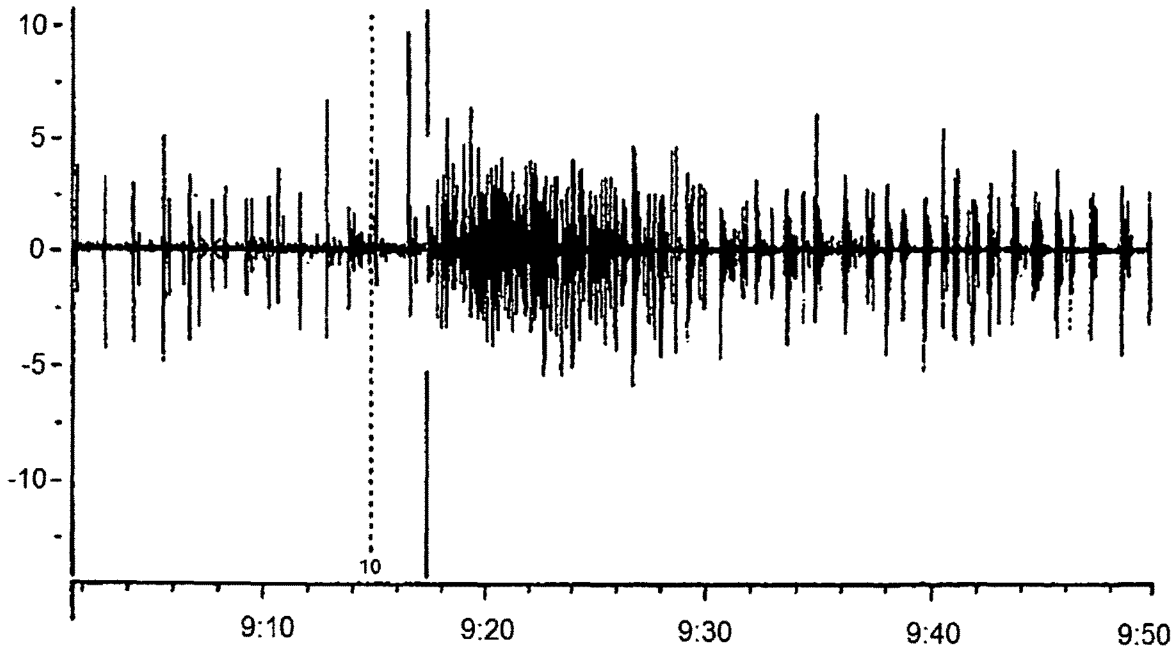
FIG. 16*a* is an EMG trace showing uterine contraction following inhalation of oxytocin delivered by example 10 formulation 3 containing 90% PVP(30) and 10% leucine. The dashed line shows the time of formulation delivery and the solid line the onset of uterine contraction. The x-axis is in hh:mm:ss and the y axis is in mV.
Figure 16B:
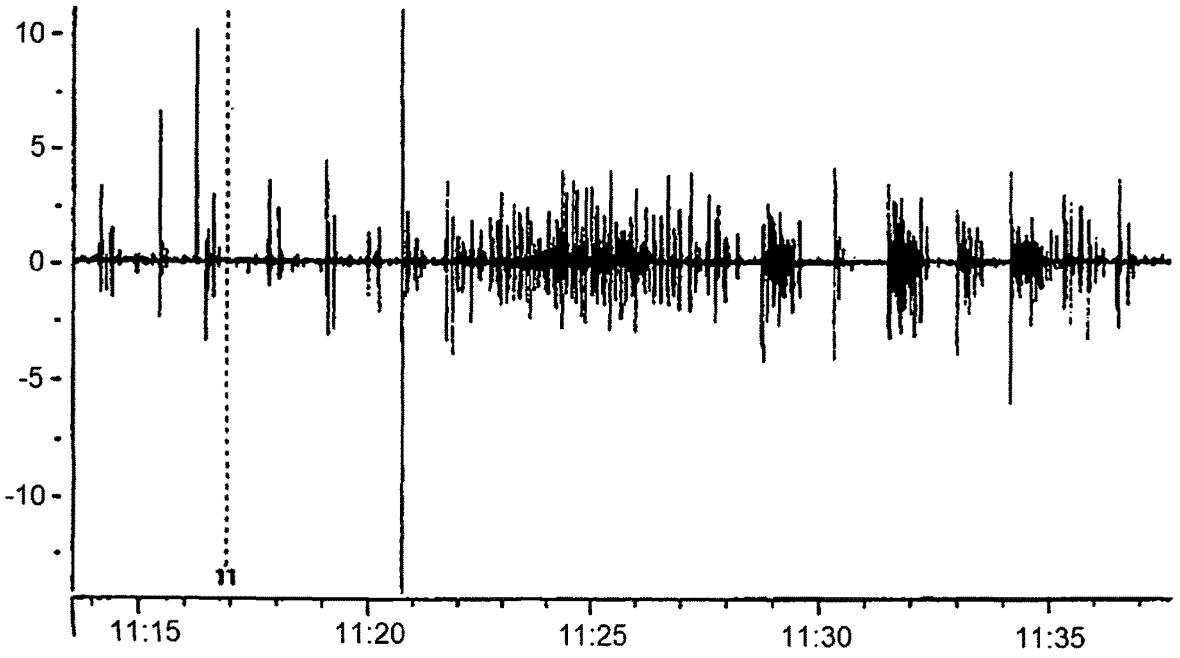
FIG. 16*b* is an EMG trace showing uterine contraction following intramuscular delivery of oxytocin (example 10 formulation 4). The dashed line shows the time of formulation delivery and the solid line the onset of uterine contraction. The x-axis is in hh:mm:ss and the y axis is in mV.

The dry powder formulations comprised spray dried compositions made as described in example 1. The compositions of these powders along with the nominal delivered dose are shown in Table 7, elapsed time (delay) from delivery of oxytocin to the initial burst of EMU activity. The delay, elapsed time from delivery of oxytocin to the initial burst of EMG activity is also shown in Table 7. EMG traces for these four doses arc shown in FIGS. 15 and 16.

TABLE 7

| Dose No | Oxytocin Dose | Mannitol % w/w | Glycine % w/w | Trehalose % w/w | PVP(30) % w/w | Leucine % w/w | Delay (s) |
|---|---|---|---|---|---|---|---|
| 1 | 200 IU | 33.3 | 33.3 | | | 33.3 | 181 |
| 2 | 200 IU | | | 90 | | 10 | 65 |
| 3 | 200 IU | | | | 90 | 10 | 150 |
| 4 | 10 IU | | 1 ml intramuscular injection | | | | 232 |

Surprisingly, the onset of action from the powder pulmonary delivery was significantly more rapid compared to intramuscular delivery, and was also consistent with the plasma versus time profiles, the data also shows that the rapid response can be attained with dry powder formulations made with a range of excipients such as polyols, sugars, amino acids and polymers. This is despite the fact that the dry powder particles contain between 10-30% leucine which is a poorly soluble and hydrophobic amino acid, which could be expected to delay dissolution. Furthermore, it is expected that a substantial proportion of the leucine will be present at the surface of the powder.

The invention has been described by way of non-limiting example only and many modifications and variations may be made thereto without departing from the spirit and scope of the invention described.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method for the treatment or prevention of post partum haemorrhage comprising administering to a subject in need thereof an inhalable dry powder, wherein said inhalable dry powder comprises spray dried particles comprising (a) oxytocin or carbetocin, (b) L-leucine, the L-leucine being present in the amount from 10 to 40% by weight based on the dry weight of said spray dried particles excluding the weight of oxytocin or carbetocin, and (c) the weight remainder of said spray dried particles being an amorphous glass matrix consisting essentially of trehalose, and the oxytocin or carbetocin being dispersed within the amorphous glass matrix, and wherein the inhalable dry powder is prepared by a process comprising: preparing an aqueous solution or suspension comprising oxytocin or carbetocin, trehalose, and L-leucine; and spray drying the aqueous solution or suspension to produce the inhalable dry powder, and the amount of dry powder administered is sufficient to provide a dose of oxytocin or carbetocin that provides an effective and rapid onset of action for treating or preventing post partum haemorrhage, and said dose is about 200 IU.

2. The method according to claim 1 wherein the inhalable dry powder is for nasal administration.

3. The method according to claim 1 wherein the inhalable dry powder is for inhalation into the pulmonary system via the mouth.

4. The method according to claim 1 wherein at least a portion of the L-leucine is located at the surface of the particles of the dry powder.

5. The method according to claim 1, wherein more than 40% of the particles of the dry powder upon inhalation have an aerodynamic diameter of less than 5 μm.

6. The method according to claim 1 wherein the oxytocin is about 1.0% of the entire powder content.

7. The method according to claim 1 wherein the spray drying is carried out at a temperature below 80° C.

8. The method according to claim 1 wherein the rapid onset of action following inhalation of the dry powder, as measured by uterine contraction, is achieved within 200 seconds of inhalation.

9. The method according to claim 8 wherein the rapid onset of action is achieved within 150 seconds of inhalation.

10. The method according to claim 9 wherein the rapid onset of action is achieved within 100 seconds of inhalation.

11. The method according to claim 1 wherein the inhalable dry powder further comprises a stabilizer.

12. The method according to claim 11 dry powder contains a stabilizer, wherein said stabilizer comprises sodium citrate.

13. The method according to claim 1, wherein the amorphous glass matrix is in an amount of 90%.

14. The method according to claim 1, wherein the amorphous glass matrix is in an amount between 80%-90% of the spray dried particles.

* * * * *